United States Patent
Krasik et al.

(10) Patent No.: US 11,006,994 B2
(45) Date of Patent: May 18, 2021

(54) COLD PLASMA GENERATING SYSTEM

(71) Applicants: Technion Research & Development Foundation Limited, Haifa (IL); Rambam Med-Tech Ltd., Haifa (IL)

(72) Inventors: Yakov Krasik, Nesher (IL); Joshua Felsteiner, Haifa (IL); Yakov Slutsker, Akko (IL); Ziv Gil, Haifa (IL); Jacob Cohen, Tel-Aviv (IL); Yoav Binenbaum, Tel-Aviv (IL)

(73) Assignees: Technion Research & Development Foundation Limited, Haifa (IL); Rambam Med-Tech Ltd., Haifa (IL)

( * ) Notice: Subject to any disclaimer, the term of this patent is extended or adjusted under 35 U.S.C. 154(b) by 253 days.

(21) Appl. No.: 15/527,499

(22) PCT Filed: Nov. 19, 2015

(86) PCT No.: PCT/IL2015/051116
§ 371 (c)(1),
(2) Date: May 17, 2017

(87) PCT Pub. No.: WO2016/079742
PCT Pub. Date: May 26, 2016

(65) Prior Publication Data
US 2017/0354453 A1    Dec. 14, 2017

Related U.S. Application Data

(60) Provisional application No. 62/081,665, filed on Nov. 19, 2014.

(51) Int. Cl.
*A61L 2/14*    (2006.01)
*A61B 18/04*   (2006.01)
(Continued)

(52) U.S. Cl.
CPC ............ *A61B 18/042* (2013.01); *A61B 1/018* (2013.01); *H05H 1/2406* (2013.01);
(Continued)

(58) Field of Classification Search
CPC .................. A61B 18/042; A61B 1/018; A61B 2017/00039; A61B 2017/00057;
(Continued)

(56) References Cited

U.S. PATENT DOCUMENTS 3,903,891 A * 9/1975 Brayshaw ............ A61B 18/042
                                              313/231.31
5,088,997 A * 2/1992 Delahuerga .......... A61B 18/042
                                              606/42
(Continued)

FOREIGN PATENT DOCUMENTS

CN    103765552    4/2014
CN    203763232    8/2014
(Continued)

OTHER PUBLICATIONS

G. Fridman, et al., Plasma Chem. Plasma Process 27, 163 (2007).
(Continued)

*Primary Examiner* — Daniel W Fowler

(57) ABSTRACT

A system for generating cold plasma is presented, suitable for use in in-vivo treatment of biological tissue. The system comprising: a control unit connectable to an elongated member at a first proximal end of the elongated member. The elongated member comprises a plasma generating unit at a second distal end thereof and gas and electricity transmission channels extending from said first proximal end towards said plasma generating unit. The control unit comprises a gas supply unit configured to provide predetermined flow rate of selected gas composition through said gas transmission channel and a power supply unit configured to
(Continued)

generate selected sequence of high-frequency electrical pulses, typically in mega Hertz range, directed through said electricity transmission channel, thereby providing power and gas of said selected composition to the plasma generating unit for generating cold plasma.

25 Claims, 27 Drawing Sheets

(51) Int. Cl.
*H05H 1/24* (2006.01)
*A61B 1/018* (2006.01)
*A61B 18/00* (2006.01)
*A61B 17/00* (2006.01)

(52) U.S. Cl.
CPC ............... *A61B 2017/00039* (2013.01); *A61B 2017/00057* (2013.01); *A61B 2017/00061* (2013.01); *A61B 2018/00791* (2013.01); *A61B 2018/00982* (2013.01); *H05H 2001/245* (2013.01); *H05H 2001/2456* (2013.01); *H05H 2001/2462* (2013.01); *H05H 2245/122* (2013.01)

(58) Field of Classification Search
CPC .. A61B 2017/0061; A61B 2018/00791; A61B 2018/00982; H05H 1/2406; H05H 2001/245; H05H 2001/2456; H05H 2001/2462; H05H 2245/122
See application file for complete search history.

(56) References Cited

U.S. PATENT DOCUMENTS

| | | | | |
|---|---|---|---|---|
| 5,130,003 | A * | 7/1992 | Conrad | C01B 13/115 204/176 |
| 5,977,715 | A | 11/1999 | Li et al. | |
| 6,099,523 | A | 8/2000 | Kim et al. | |
| 6,213,999 | B1 * | 4/2001 | Platt, Jr. | A61B 18/042 606/27 |
| 6,565,558 | B1 | 5/2003 | Lindenmeier et al. | |
| 6,958,063 | B1 | 10/2005 | Soll et al. | |
| 7,316,682 | B2 | 1/2008 | Konesky | |
| 7,572,998 | B2 | 8/2009 | Mohamed et al. | |
| 7,608,839 | B2 | 10/2009 | Coulombe et al. | |
| 7,785,322 | B2 | 8/2010 | Penny et al. | |
| 8,077,094 | B2 | 12/2011 | Anderson et al. | |
| 8,187,265 | B2 | 5/2012 | Choi et al. | |
| 8,232,729 | B2 | 7/2012 | Kitano et al. | |
| 8,725,248 | B2 | 5/2014 | Gutsol et al. | |
| 2001/0000206 | A1 | 4/2001 | Li et al. | |
| 2005/0118350 | A1 * | 6/2005 | Koulik | A61B 18/042 427/535 |
| 2010/0100094 | A1 * | 4/2010 | Truckai | A61B 18/042 606/39 |
| 2011/0112528 | A1 | 5/2011 | Stieber et al. | |
| 2012/0029506 | A1 | 2/2012 | Johnson | |
| 2012/0107896 | A1 | 5/2012 | Wandke et al. | |
| 2012/0245580 | A1 * | 9/2012 | Germain | A61B 18/042 606/41 |
| 2012/0283732 | A1 | 11/2012 | Lam | |
| 2012/0288405 | A1 * | 11/2012 | Snowball | A23L 3/34095 422/22 |
| 2012/0289954 | A1 | 11/2012 | Lam | |
| 2013/0053762 | A1 | 2/2013 | Rontal et al. | |
| 2013/0199540 | A1 * | 8/2013 | Buske | A61B 18/042 128/845 |
| 2014/0005646 | A1 * | 1/2014 | Temelkuran | A61B 18/201 606/14 |
| 2014/0074090 | A1 | 3/2014 | Lam et al. | |

FOREIGN PATENT DOCUMENTS

| | | |
|---|---|---|
| EP | 0694290 | 1/1996 |
| WO | 2012/153332 | 11/2012 |
| WO | 2012/167089 | 12/2012 |
| WO | 2014/061025 | 4/2014 |

OTHER PUBLICATIONS

J. Schlegel, et al., Clinical Plasma Medicine 1, 2 (2013).
E. Robert, et al., Clinical Plasma Medicine 1, 8 (2013).
M. Keidar et al., Br. J. Cancer, 105, 1295 (2011).
Adam M. Hirst, et al., BioMed Research International, vol. 2014, Article ID 878319.
Low temperature plasma biomedicine: A tutorial review, to David B. Graves, Physics of Plasmas (1994-present) 21, 080901 (2014); doi: 10.1063/1.4892534.
International Search Report for International Application No. PCT/IL2015/051116 dated Feb. 22, 2016.
Notification of Office Action and Search Report dated May 22, 2019 From the China National Intellectual Property Administration Re. Application No. 201580069489.0 and Its Translation Into English. (18 Pages).
Notification of Office Action and Search Report dated Dec. 25, 2020 From the State Intellectual Property Office of the People's Republic of China Re. Application No. 201580069489.0 and Its Translation of Office Action Into English. (11 Pages).

* cited by examiner

NTP Tx
(1Tx/week)

62,608 Pixels

Control
No NTP Tx 120,868 Pixels

COLD PLASMA GENERATING SYSTEM

TECHNOLOGICAL FIELD

The invention relates to systems and method for producing cold plasma and is particularly relevant for use in medical application.

BACKGROUND ART

References considered to be relevant as background to the presently disclosed subject matter are listed below:

G. Friedman, et al., [Plasma Chem. Plasma Process 27, 163 (2007)];
J. Schlegel, et al., [Clinical Plasma Medicine 1, 2 (2013)];
E. Robert, et al., Clinical Plasma Medicine 1, 8 (2013)];
M. Keidar et al., [Br. J. Cancer, 105, 1295 (2011) and Phys. Plasma 20, 057101 (12013)];
Adam M. Hirst, et al BioMed Research International, Volume 2014, Article ID 878319;
Low temperature plasma biomedicine: A tutorial review, to David B. Graves, Physics of Plasmas (1994-present) 21, 080901 (2014); doi: 10.1063/1.4892534.

Acknowledgement of the above references herein is not to be inferred as meaning that these are in any way relevant to the patentability of the presently disclosed subject matter.

BACKGROUND

Plasma is a general term defining ionized gas, generally including free electrons, ions as well as neutral atoms and molecules and often free radicals. It may be produced by electric discharge through gas, causing gas atoms or molecules to be excited and ionize. During the past decade significant interest in plasma applications has grown. Various such applications are based on Dielectric Barrier Discharge (DBD) for generation of the non-thermal plasma of low temperature, or so-called "cold" plasma. Such cold plasma is a low-ionized and non-thermal plasma generated at atmospheric pressure conditions. It has been found that cold plasma can be used for various applications in medicine and industry.

General background information concerning generating techniques for cold plasma and some medical applications thereof can be found in the following patent publications relating to background data of the present invention:

U.S. Pat. No. 8,232,729 Plasma producing apparatus and method of plasma production
U.S. Pat. No. 8,187,265 Coagulation apparatus using cold plasma
U.S. Pat. No. 8,077,094 Plasma device with low thermal noise
U.S. Pat. No. 7,785,322 Tissue resurfacing
U.S. Pat. No. 7,572,998 Method and device for creating a micro plasma jet
U.S. Pat. No. 7,316,682 Electrosurgical device to generate a plasma stream
U.S. Pat. No. 6,958,063 Plasma generator for radio frequency surgery
U.S. Pat. No. 6,565,558 High-frequency device for generating a plasma arc for the treatment of biological tissue
U.S. Pat. No. 6,099,523 A Cold plasma coagulator
U.S. Pat. No. 3,903,891 Method and apparatus for generating plasma
US 2001/0000206 Surface modification using an atmospheric pressure glow discharge plasma source
WO 2014/061025 Films, kits and methods for enhancing tissue treatment by plasma welding
US 2014/0074090 Tissue welding using plasma
US 2012/0283732 Plasma head for tissue welding
US 2012/0289954 Micro plasma head for medical applications
U.S. Pat. No. 8,725,248 Methods for non-thermal applications of gas plasma to living tissue
WO 2012/167089 System and method for cold plasma therapy
US 2011/0112528 plasma device for selective treatment of electropored cell
U.S. Pat. No. 7,608,839 Plasma source and applications thereof
U.S. Pat. No. 5,977,715 Handheld atmospheric pressure glow discharge plasma source

GENERAL DESCRIPTION

There is a need in the art for a novel technique for generating cold plasma for use in medical applications on living biological tissue. The technique of the present invention provides a system suitable for generating a selected sequence of cold plasma bursts in a very close proximity to biological tissue. The plasma bursts may be applied on tissue being inside an existing natural cavity, artificial/man-made cavity or external tissue. The inventors of the present invention have found that applying cold plasma of suitable characteristics when applied on the desired tissue can be used for treatment of various types of cancer and other medical applications.

Cold plasma can generally be generated by Dielectric Barrier Discharge (DBD) technique. DBD plasma generation can be realized by application of a high-voltage (HV) pulse through a gas-filled gap between two electrodes, when one or both electrodes are covered with a dielectric material. This typically results in a non-complete electrical discharge through the gas, which is characterized by a discharge current of electrons in the gas-filled gap, and displacement current through the dielectric material.

To allow suitable discharge current (i.e. to develop a DBD) the mean free path of the primary electrons should be sufficiently long in order to allow the electrons to acquire sufficient energy from the electric field. When the energetic electrons collide with gas atoms/molecules, the electrons may cause ionization of gas particles. These primary electrons could be either emitted from the surface of the negative (cathode) electrode, if not covered by dielectric layer. Alternatively, in the case that both anode and cathode electrodes are covered by dielectric layer, the electric field accelerates electrons that naturally exist in the gas within the gap. Typically the density of free electrons in appropriate gas composition is in the range $10^3$-$10^4$ in $cm^3$.

Typically, dielectric barrier discharge (DBD) current flows only when the electric field is time varying, i.e. the derivative $dE/dt \neq 0$ is not null, where E is the electric field and t is time. This is because a closed path for current in the corresponding electrical circuit is required to support flow of electrons in the gas by displacement current $j_d \propto d\varphi/dt$, where $j_d$ is the displacement current and $\varphi$ is the potential difference in the gap between the electrodes. This indicates that rectangular pulse shape, being of any voltage, can emit DBD current only during the rise and fall time of the pulse.

Efficient plasma generation may utilize electric pulses having alternating polarity. Due to higher mobility of plasma electrons (relative to the ions) they attach to the anode (typically dielectric) surface when electric field polarity directs negative charge to the cathode. These electrons screen the external electric field. When the opposite polarity of the pulse is applied, i.e. the anode becomes the cathode; these electrons are detached from the dielectric surface and serve as a source of electrons for gas ionization. At the discharge stage, the free plasma electrons attach again to the dielectric surface of the anode (i.e. the one which was the cathode during the first part of the discharge) allowing the cycle to renew in the following pulse.

The plasma that forms between the electrodes typically acquires a positive potential with respect to both electrodes, due to the lower mobility of the ions relative to the electrons. The value of this potential depends on parameters of the pulse and the resulting electric discharge (e.g. voltage, current amplitude, pulse waveforms, type and pressure of the gas) and on the geometry of the electrodes.

Typically, in conventional "cold" plasma formation and propagation techniques, small stray capacitance is maintained between the plasma and the ground potential. This small value of stray capacitance maintains a large potential at the plasma gun. However, when the capacitance between the plasma generating electrode and ground electrode is increased, generation of the plasma may be terminated, and the potential difference between the electrodes at the plasma gun decreases. As a result, the electric field at the plasma generating head (plasma gun) becomes lower and cannot support electron avalanching through the gas. This configuration renders plasma use within or on living biological tissue somewhat dangerous, as both electrodes are configured with high voltage with respect to the ground.

Indeed, various techniques for medical plasma applications are known, typically focusing on external treatment, or generating the plasma at a remote location and transmitting it towards the desire tissue. Such applications suffer from high termination rate of the propagating plasma, due to interactions with the tube/catheter (which is typically a dielectric tube). This provides a tube length of a few centimeters or less.

The inventor of the present invention have found that utilizing the self impedance of the cable transmitting electric signals and the electrodes of the plasma gun in determining electric pulse characteristics solves this charge accumulation problem. Additionally, the inventors have found that the use of coaxial electricity transmission channel can provide both shielding of the high voltage signals from the tissue surrounding the cables, as well as known impedance (capacitance) values and prevents emission of electromagnetic radiation generated by the varying pulses. The above features, separately or in combinations enable the plasma generating system described herein to be safely used within cavities of living patients (human and/or animals).

The technique of the present invention thus provides a novel configuration of plasma generating system, enabling the use of cold plasma within a living biological cavity (e.g. suitable for endoscopic applications). To this end the technique of the present invention provides for delivering high-frequency and high-voltage electric pulses to the vicinity of a desired location for local generation of cold plasma with high carrier frequency of the input power/pulses, while eliminating, or at lease significantly reducing the risk of electrocution and/or leakage of electromagnetic radiation generated by the high frequency (e.g. radio frequency (RF)) pulses.

In this regard, the technique of the invention enables control of plasma flow rate and temperature. This may be done by controlling repetition rate of the electric signals/pulses generating the plasma, voltage profile (peak voltage and pulse width) of the pulses and flow rate of the gas. Control of these parameters allows fine tuning of the plasma properties to provide controlled desired results suitable for treatment of biological tissue. The inventors of the present invention have found that applying plasma of predetermined specific properties onto biological tissue may selectively affect cancerous cells while minimally affecting healthy cells. This is while lower density plasma would not provide such effect. Importantly, plasma of higher density or temperature may damage healthy cells and effectively burn the tissue.

To this end, the technique of the present invention utilizes generation of a selected sequence of high-frequency electric pulses (typically within the Mega Hertz range) and transmitting the corresponding electrical signals along an electricity transmission channel towards a plasma generating unit. The plasma generating unit may be located as a distal end of an elongated member, e.g. endoscope like element. The use of high-frequency pulses enables reduction of peak voltage of the pulses to be no more than a few Kilo-Volts, while still allowing generating of plasma at typical temperature lower than a threshold for protein denaturation. For example, the present technique utilizes plasma with characteristic temperature of about 40° C. (or typically between 25° C. and 50° C.). Further, the electricity transmission channel is preferably configured to provide shielding of electricity conduction from the surrounding, thus eliminating, or at least significantly reducing any risk of short circuit between the transmission channel and any biological tissue in its vicinity. The transmission channel may also be configured to eliminate or at least significantly reduce any leakage of electromagnetic radiation that may be formed due to the high-frequency electric signals transmission through the channel. To this end the electricity transmission channel is preferably configured as a coaxial cable comprising an inner conductor transmitting the electrical signal and a grounded external conductor configured for closing the circuit as well as shielding the inner conductor. The use of coaxial cable for electricity transmission channel, while serving a part of the pulses generating circuit of the power supply unit, eliminates leakage of electromagnetic radiation and the use of grounded external conductor eliminates or at least significantly reduces the risk of electric short circuit with the biological tissue. The electricity transmission channel it typically defined as having self-impedance (capacitance, inductance and resistance) for transmission of electrical signals.

In addition to transmitting electric signals, the technique of the invention utilizes a gas transmission channel, extending together with the electricity transmission channel towards the plasma generating unit. Transmission of the appropriate gas (e.g. Penning mixture, Helium, Nitrogen, Oxygen or a mixture thereof) may be continuous or pulse like. This is while suitable plasma (cold plasma) is generated only in the presences of sufficient amount of gas in combination with varying portion of the electric pulse.

Thus, the present invention provides a plasma generating system, configured for generating cold plasma for local treatment of biological tissue (e.g. endoscopy-like treatment as well as external tissue treatment). The system utilizes a plasma generating unit mounted on a distal end of an elongated, typically flexible, member that is connected on its proximal end to a control unit. The elongated member comprises gas and electricity transmission channels configured for providing gas mixture and electric signals for operating the plasma generating unit.

The control unit comprises a gas supply unit and a power supply unit. Generally the control unit may also include a user control interface enabling an operator to determine operation properties of the system. The power supply unit is configured to generate a selected sequence of high-frequency electric pulses to be transmitted through the electricity transmission channel and operate the plasma generating unit for generation of cold plasma.

The power supply unit may for example comprise an RF oscillator circuit configured for generating high-frequency electric pulses. The circuit may be based on a vacuum tube (e.g. vacuum electron tube EL34) or any other amplifying element such as transistor, capable of operating in MHz frequency range. Additionally, the oscillator resonance circuit may be configured in accordance with impedance of the electricity transmission channel as well as the plasma generating unit in order to support high-frequency pulses with predetermined frequency and optimal amplitude. As indicated above, the power supply is configured for generating pulses with based frequency between 0.5 MHz and 10 MHz and peak-voltage between 0.5 kV and 6 kV, and preferably between 0.75 kV and 1.15 kV. In some configuration the pulse sequence may include electrical pulses with repetition rate of 100 Hz to 600 Hz while the pulses are characterized by having carrier frequency of 0.5 MHz to 10 MHz, and preferably within a range around 1.5 MHz (e.g. 1 MHz to 2 MHz).

In some configuration, the power supply unit is configured such that the electricity transmission channel is directly connected to an external inductor having inductance L that is significantly higher the inductance of the electricity transmission channel. This provides that main resonant frequency of the oscillator circuit to be determined based on a classic resonance of an LC circuit, where C is the total effective capacitance in the circuit, which is largely the capacitance of the electricity transmission channel. This is while the inductance of the channel is negligible with respect to inductance L of the inductor. Thus the electrical length of the electricity transmission channel may be significantly smaller than the pulse duration.

As indicated above, the plasma generating system described herein is configured for generating cold plasma suitable to treatment of biological tissue, being internal or external to the body. More specifically, the cold plasma may be applied externally on exposed tissue or internally, e.g. utilizing and endoscope, through or alongside which, the elongated member (including the gas and electricity transmission channels) is conducted. Application of cold plasma generated according to the present technique exposes the tissue to free electrons and charged ions and radicals, affecting cancerous cells at a higher degree than healthy cells. Thus, the present technique enables local treatment of biological tissue in living organisms, e.g. human and animals.

Thus, according to one broad aspect of the present invention, there is provided a system for generating cold plasma. The system comprising a control unit connectable to an elongated member at a first proximal end of the elongated member; said elongated member comprises a plasma generating unit at a second distal end thereof and gas and electricity transmission channels extending from said first proximal end towards said plasma generating unit; the control unit comprises a gas supply unit configured to provide predetermined flow rate of selected gas composition through said gas transmission channel and a power supply unit configured to generate selected sequence of high-frequency electrical pulses directed through said electricity transmission channel, thereby providing power and gas of said selected composition to the plasma generating unit for generating cold plasma.

The power supply unit, electricity transmission channel and plasma generation unit may be configured to prevent electrical discharge into surrounding thereof, thereby enabling use of said plasma generating unit on live biological tissue.

According to some embodiments, said selected sequence of high frequency electrical pulses may consist of a sequence of pulses having repetition rate between 100 Hz and 600 Hz, carrier frequency between 500 kHz and 10 MHz and having peak voltage between 0.5 kV and 2 kV. The selected sequence of high frequency pulses may also consist of a sequence of pulses having pulse duration between 400 and 800 milliseconds.

According to some embodiments of the invention, the electricity transmission channel is configured for preventing electricity discharge and electromagnetic radiation into surrounding thereof to thereby prevent damage to surrounding biological tissue. For example, the electricity transmission channel may be configured as a coaxial electricity transmission cable having an internal conductor configured to carry electricity signal and an external conductor shielding between electrical potential in said internal conductor and surrounding of the cable; said external conductor may be kept at ground potential.

According to some embodiments, said electricity transmission channel is characterized by predetermined impedance, the power supply unit may comprise a resonance circuit configured for generating said high frequency pulses, resonant frequency of said resonance circuit being determined in accordance with said predetermined impedance of the electricity transmission channel.

According to some embodiments the gas supply unit may be configured to supply a desired or predetermined flow of gas along said gas transmission channel, thereby providing said gas mixture having low breakdown threshold. In some embodiments, said gas comprises penning mixture. In some embodiments said penning gas mixture is a mixture of Neon and Argon gasses with ratio between 98:2 and 99.9:0.1 of Ne:Ar. In some other embodiments said gas comprises Helium, Nitrogen and/or oxygen.

Generally, according to some embodiments, said elongated member, including said gas and electricity transmission channels thereof, may be flexible. In some configuration the elongated member may comprise a flexible portion and a rigid portion. For example, the elongated member generally comprises a distal portion; said distal portion may be rigid thereby enabling direction of the distal end to a desired location.

Additionally or alternatively the elongated member may be configured to be inserted into a working channel of an endoscope for selectively generating cold plasma within a cavity of a biological tissue.

In some embodiments, the elongated member may further comprise one or more additional sensors mounted at said second distal end thereof, said one or more additional sensors comprise at least one of the following: thermal sensor, spectrometry sensor, optical sensor, photo-spectrometer sensor, electric field sensor and magnetic field sensor. For example, a photo-spectrometer sensor may be configured for detecting hydroxyl radicals generated from interaction of the cold plasma with biological tissue.

According to some embodiments of the invention, the plasma generating unit (or plasma gun) is configured as dielectric barrier discharge plasma generating unit and comprising a first internal electrode providing electrical potential and a second external electrode, at least one of said first and second electrode is covered by a dielectric layer of predetermined thickness; potential difference between said first and second electrodes cause electrical discharge through gas flowing between said first and second electrodes to thereby generate said plasma. The plasma generating unit, when operated with input gas and electric pulses, may be configured to generate plasma plume having an effective range between 2 mm and 20 mm.

The plasma generating system, according to some embodiments of the invention may be configured for generating cold plasma being characterized in having temperature below 50° C. The system may be configured for use in treatment of cancer in living tissue. For example, the elongated member may be configured to be directed to apply cold plasma at natural or surgically made cavities in living organisms.

According to some embodiments of the invention, the elongated member comprises a coaxial cable having metallic (e.g. silver) coated inner and outer electrodes, and a insulation between them, thereby providing negligibly small energy losses and drastically reducing heating of the cable while allowing it to be safely placed inside a living body. According to some embodiment, the plasma generating unit (plasma gun) comprises a first inner metallic coated electrode and a second outer electrode, thereby providing efficient plasma generating while eliminating or at lease significantly reducing electric discharge into the surrounding while allowing discharge within the input gas for generating cold plasma.

According to a further broad aspect of the invention, there is provided a method for generating cold plasma within a biological cavity, the method comprising: providing a flow of gas of predetermined material composition and predetermined flow rate through an elongated transmission channel to a desired location within said biological cavity; generating a series of selected sequence of high frequency electrical pulses and transmitting said series through a shielded electricity transmission channel to said desired location; allowing discharge of potential difference resulting from said series of high frequency electrical pulses through said gas flow at close proximity to said desired location with the biological cavity, thereby generating cold plasma flow directed at said desired location.

Said generating a series of selected sequence of high frequency electrical pulses may comprise utilizing a resonance circuit having resonant frequency between 0.5 MHz and 10 MHz, said resonance frequency being determined in accordance with impedance of the shielded electricity transmission channel.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 2F illustrates a block diagram of the power supply unit;

DETAILED DESCRIPTION OF EMBODIMENTS

Figure 1A:
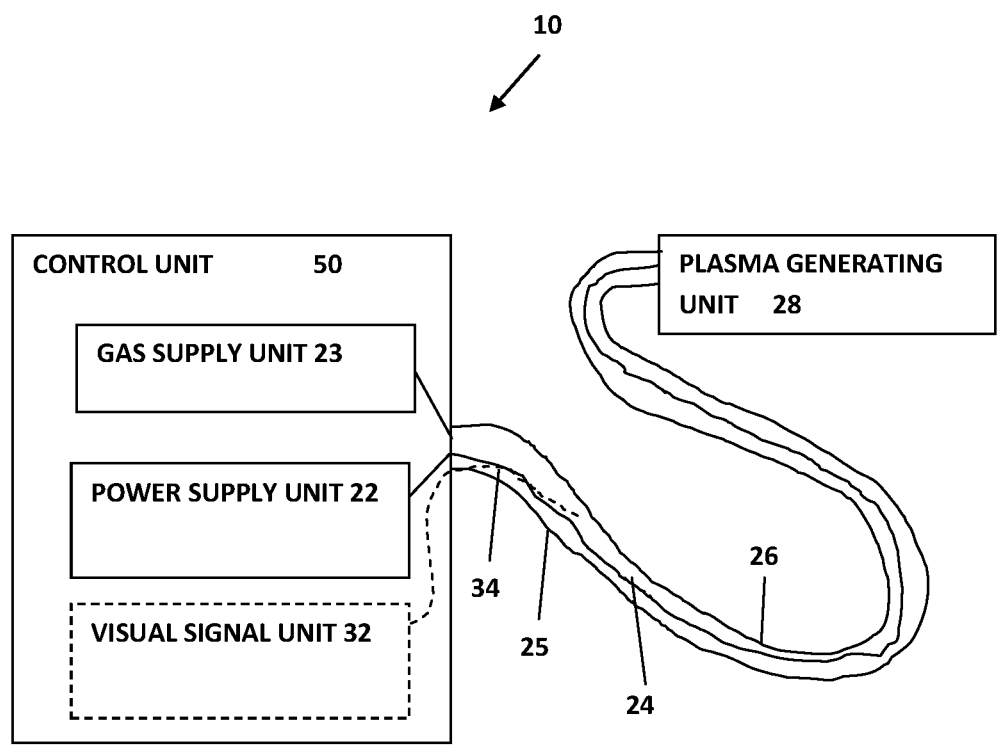
FIGS. 1A and 1B illustrate a plasma generating system according to some embodiments of the present invention.
Figure 1B:
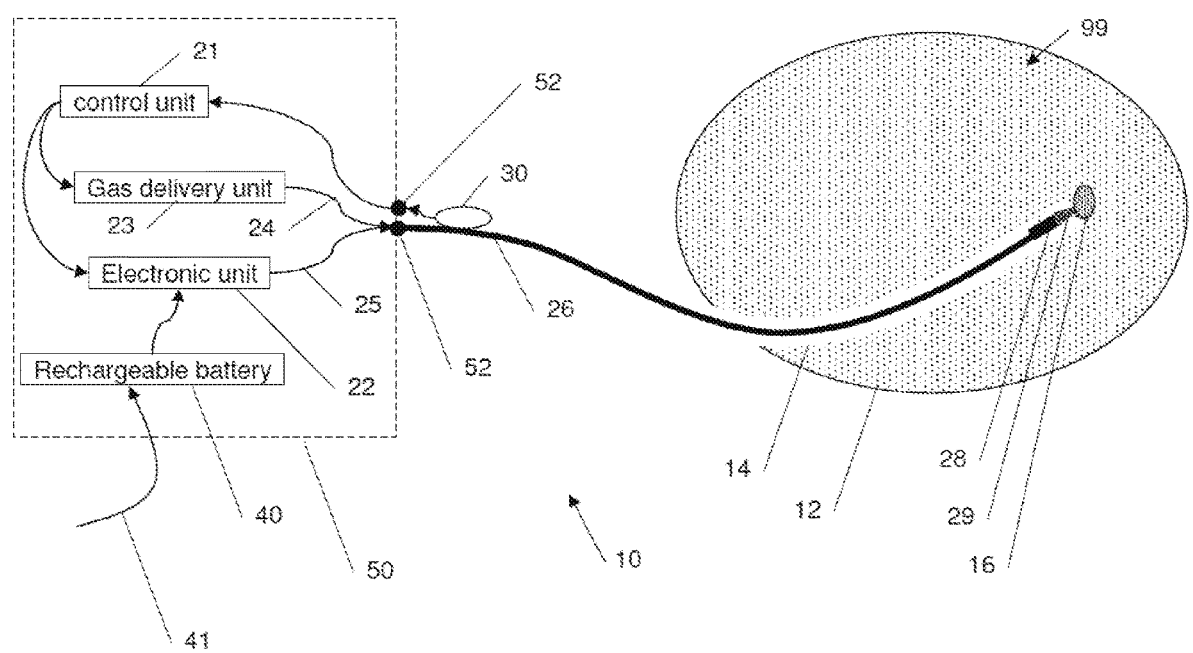

As indicated above, the present invention provides a system and method for use in local application of cold plasma on biological tissue. Reference is made to FIG. 1A and FIG. 1B, both exemplifying a plasma generating system 10 according to some embodiments of the invention. The system 10 typically includes control box 50 including a control user interface and at least gas 23 and power 22 supply units. The control unit 50 is connectable to an elongated member 26 including at least gas 24 and electricity 25 transmission channels configured for transmitting gas and electric signals from the control unit 50 at a proximal end of the elongated member 26 to a plasma generating unit 28 mounted on a distal end thereof. The control box 50 may also include a visual signal unit 32 configured to transmit light through an optical fiber 34 and receive visual input coming back through the fiber 34. This enables an operator to receive visual input about location of the plasma generating unit 28 at the distal end of the elongated member 26 for use as endoscope.

The elongated member 26 may typically configured to be flexible and enable a user to direct the plasma generating unit 28 to apply plasma on a selected location. Additionally, in some configurations, the elongated member 26 may be configured for use as an endoscope. More specifically the member 26 may be configured to be inserted into an existing of manufactured cavity in a body (e.g. human or animal body) and locally apply cold plasma onto selected points within the cavity.

In this connection, the inventors have found that application of cold plasma, in temperature between 25° C. and 60° C. so as not to cause denaturation of proteins, on cancer cells, damage the cells while leaving healthy tissue cells mostly unaffected. However, the inventors have further understood that generating plasma at a remote (a few centimeters or more) location and transferring the plasma towards the desired tissue results largely in degradation of the plasma due to interaction with the transmission channel. For example, charged ions and radicals may interact with tube walls thereby destroying the plasma state of the gas. Alternatively, generating the plasma by electric discharge at vicinity of the desired location might be dangerous in application on living organisms due to the high voltage required for the discharge.

The system of the present invention is thus configured for locally generating cold plasma of desired characteristics (e.g. temperature, density) while eliminating the risk of electric shock to a living organism (human or animal) being treated thereby. This is achieved according to the technique of the invention by at least one of the following: utilizing high-frequency low voltage electric pulses for activating the plasma generating unit 28 for discharge; utilizing a shielded configuration of the electricity transmission channel 25, which is also a part of the resonance circuit as will be described in more details further below. This allows the system to be configured for use to apply cold plasma in cavities (natural or manufactured) in living organism bodies.

More specifically, the use of high-frequency electric pulses enables the plasma generating unit 28 to create appropriate electric discharge at relatively low voltages. Specifically, at pulse frequency between 0.5 MHz and 10 MHz electric discharge can be achieved at peak voltage as low as 5-6 kV and even at voltage of 1 kV or 750V. These high-frequency low voltage pulses provide that even if electric short circuit is caused with the biologic tissue, the electric power of the pulse is sufficiently low to avoid damage to the tissue.

Additionally or alternatively, the electricity transmission channel may be configured such to eliminate or at lease significantly reduce the risk of electric short circuit with biological tissue. This may be achieved by providing the electricity transmission channel with a first signal conductor shielded by a second ground conductor separating between the first conductor and the surrounding. Additionally, the plasma generating unit 28 may be configured with an internal signal electrode and an external ground/zero electrodes closing the circuit while shielding the electric signal from the surrounding.

Similarly, FIG. 1B exemplified another configuration of the cold plasma generating and treatment system 10. The system 10 is typically configured for cold plasma treatment within a tissue cavity 14 of a patient 99 (living human or animal). The system includes a main control box 50 connectable to an elongated flexible probe 26 (elongated member) at a proximal end of the probe 26. The elongated probe 26 is attached to a plasma generating unit 28 at distal end thereof.

The control box 50 includes a control unit 21 configured with an interface panel (not shown) for operating the system. Further the control box includes a gas supply/delivery unit 23, which may generally include a compressed gas reservoir (e.g. a tank with compressed gas) or a connection to a remote reservoir. Generally the gas supply unit 23 is configured to supply gas of predetermined material composition. In some embodiments, the gas may be selected as having low ionization potential, i.e. configured to be ionized with low discharge potential, such as Penning mixture. Such gas composition may include Neon (Ne) and Argon (Ar) at predetermined ratio. However it should be noted that any gas or gas mixture may be used, for example Helium (He) or air mixture including Nitrogen ($N_2$) and Oxygen ($O_2$). In some additional configuration, the gas supply unit 23 may be configured with connection to a plurality of tanks with compressed gases and a gas manifold to switch between gases or to select a mixture of gases. The gas supply unit 23 may typically also include a pressure reduction regulator, valves and other elements as known in the art for controlling and monitoring gas flow.

Additionally, the system 10 includes an electronic unit 22 also referred to herein as power supply unit. Electronic unit 22 includes an electronic circuit configured for generating and delivering Radio Frequency (RF) electric pulses for creating plasma at the plasma generating unit 28 (plasma head) located at the distal end of probe 26. Generally the power supply unit 22 may include an amplified resonance circuit for generating a selected sequence of pulses as will be described further below. The power supply unit 22 is connectable to transmit the electric pulses to the plasma generating unit 28 through an electricity transmission channel 25 extending within and along the probe 26. The electricity transmission channel 25 may preferably be configured as a coaxial cable having a first internal conductor surrounded by a second external conductor such in a cylindrical symmetry about a common axis. In some embodiments, the electricity transmission channel is configured such that the first internal conductor is the signal line while the second external conductor closes the circuit. Additionally, the closed circuit may be such that the second external conductor is held at ground potential to provide shielding and prevent electric shock to a patient 99.

The control box 50 and the control interface 21 thereof provide an operator with access for controlling the plasma generating system 10. To this end the control interface 21 typically include switches and controls allowing individual or simultaneous operation of the gas flow from the gas supply unit 23 and RF electrical pulses from the power supply unit 22. The control interface may include various additional controls such as determining pulse duration, duty cycle, amplitude, a number of pulses in a sequence etc. Additionally the control interface may include selection of gas composition, gas flow rate and pressure etc., directing and control of location of the distal end of the probe 26 and the plasma generating unit 28 thereon. The control interface 21 may generally also include access to safety measures enabling emergency shut down of the system in automatic and/or manual modes.

As described above, the gas 23 and power 22 supply units are respectively connected to the gas 24 and electricity 25 transmission channels. The gas transmission channel 24 is typically configured as a gas pipe extending along the probe/elongated member 26 from its proximal end towards the plasma generating unit 28 at the distal end. Additionally the electricity transmission channel 25 is, as indicated above, configured to eliminate or at least minimize a risk of electric short circuit with tissue of the surrounding of the probe. To this end, the electricity transmission channel 25 may be configured as a coaxial cable, where the internal conductor transmits the electric signals and the external conductor closed the circuit. In some embodiments, the external conductor of the coaxial cable is grounded to thereby provide additional shielding of the surrounding.

The elongated member 26 or probe is configured for connecting the control box 50 and the various units thereof and supply electric power and gas to the plasma generating unit 28. In some configurations, the elongated member 26 may simply be a bundle of the cables defining the transmission channels. The probe 26 may also be configured as a flexible catheter that can be inserted into body lumens or cavities 14 such as the urinary tracts, the digestive systems, the bronchial tree as etc., as well as artificial cavities, such that the distal end thereof, carrying the plasma generating unit 28 can locally apply cold plasma within body cavity. To this end the distal end of the probe 26 may also include one or more sensor elements such as temperature sensor, biological sensor of any type and optical sensing such as optical fiber and/or camera(s). Thus the probe 26 and plasma generating unit 28 may be used during operations such as in laparoscopy, pleural procedures, joint replacements, etc. as well as in general procedures, to locally apply cold plasma to desired location. In some configurations however, the probe 26 and plasma generating unit 28 at the distal end thereof may be configured to apply cold plasma externally to a body.

Also, it should be noted that the distal end of the probe 26, and the plasma generating unit 28 mounted thereon are preferably configured with a rigid end. This is to enable a use in endoscopic procedures.

In some configuration, a command unit 30 associated with the interface panel 21 may be mounted on the probe 26 to simplify access for operation commands.

Also, in may be noted that the plasma generating system 10 may be configured with relatively low power requirements as it may operate with high-frequency low voltage pulses for plasma generation. Thus, the system may utilize a battery 40 (rechargeable or not) as power source, or be connected to the grid 41.

It should also be noted that the probe 26 of the plasma generating system 10 described herein may be used as an endoscope by itself, as described above, or may be configured to be attached/inserted into an existing endoscope. This may simplify the configuration of the system while enabling flexibility in utilizing cold plasma application in combination with one or more additional surgical operations using endoscopes.

Figure 2A:
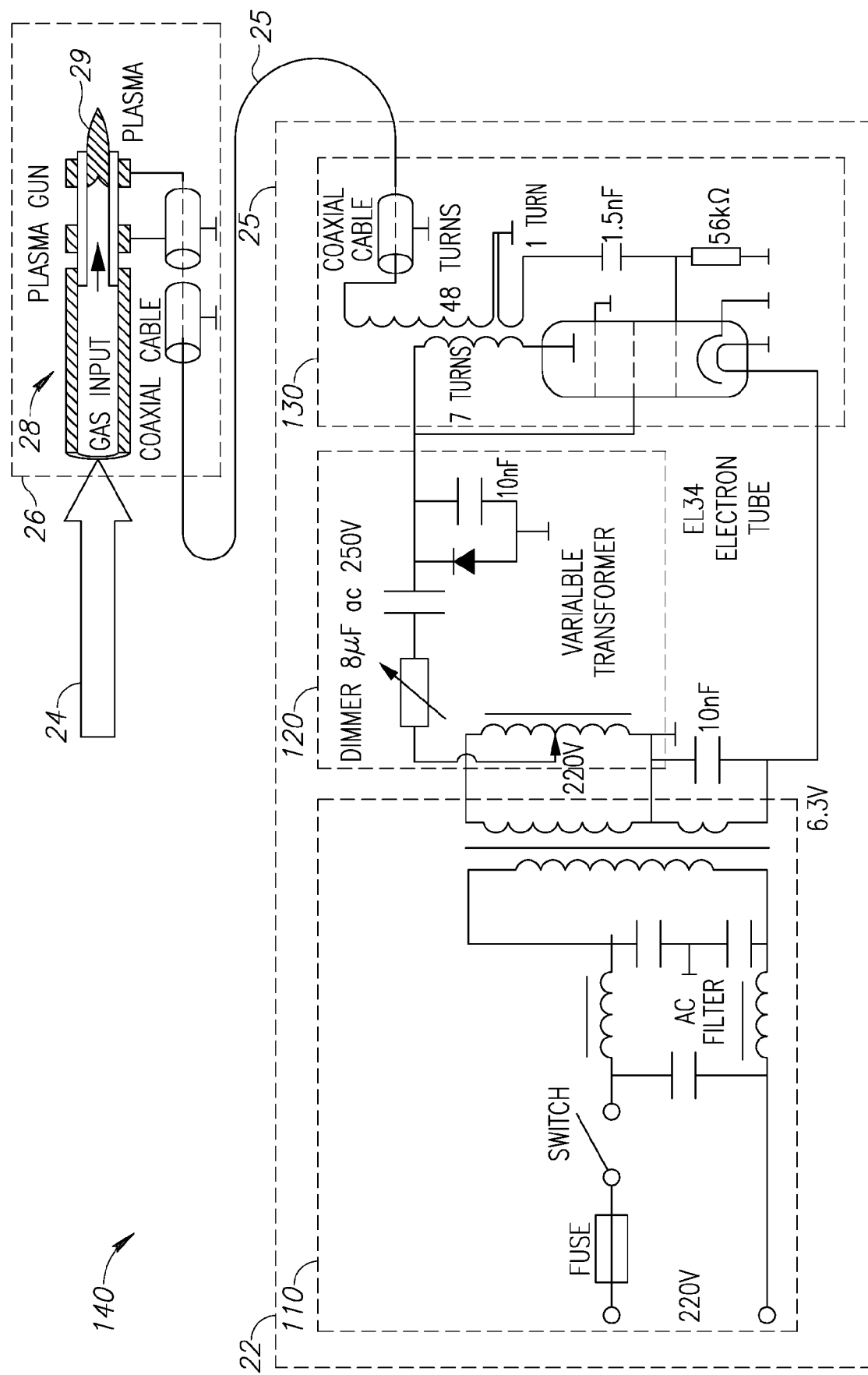
FIGS. 2A to 2F schematically illustrate electronic configuration of a power supply unit for use on a plasma generating system according to some embodiments of the invention, FIGS. 2A to 2E exemplify configuration of the power supply unit
Figure 2B:
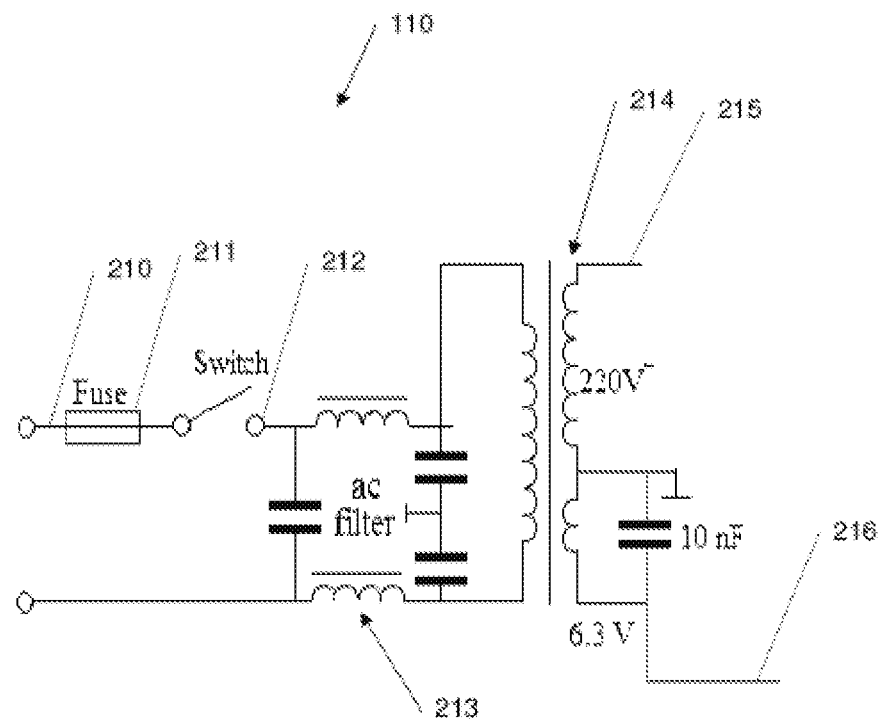
Figure 2C:
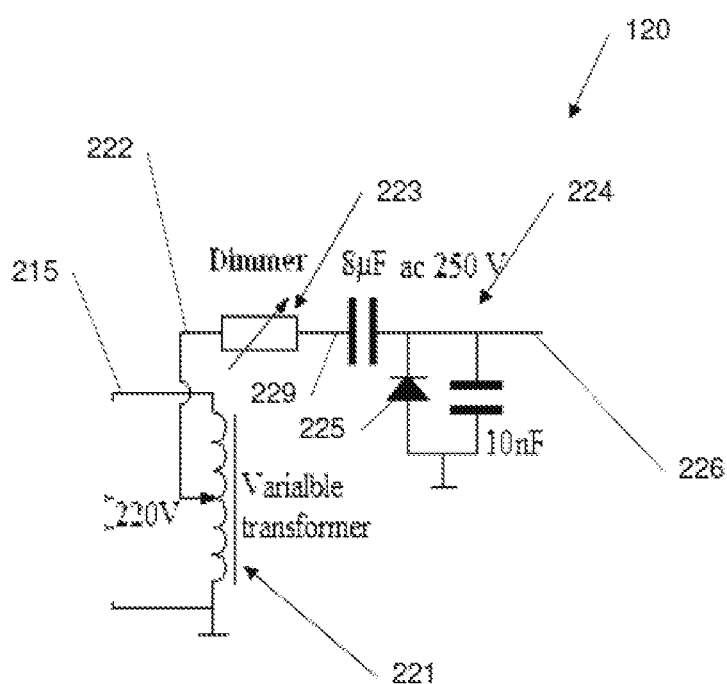
Figures 2D, 2E:
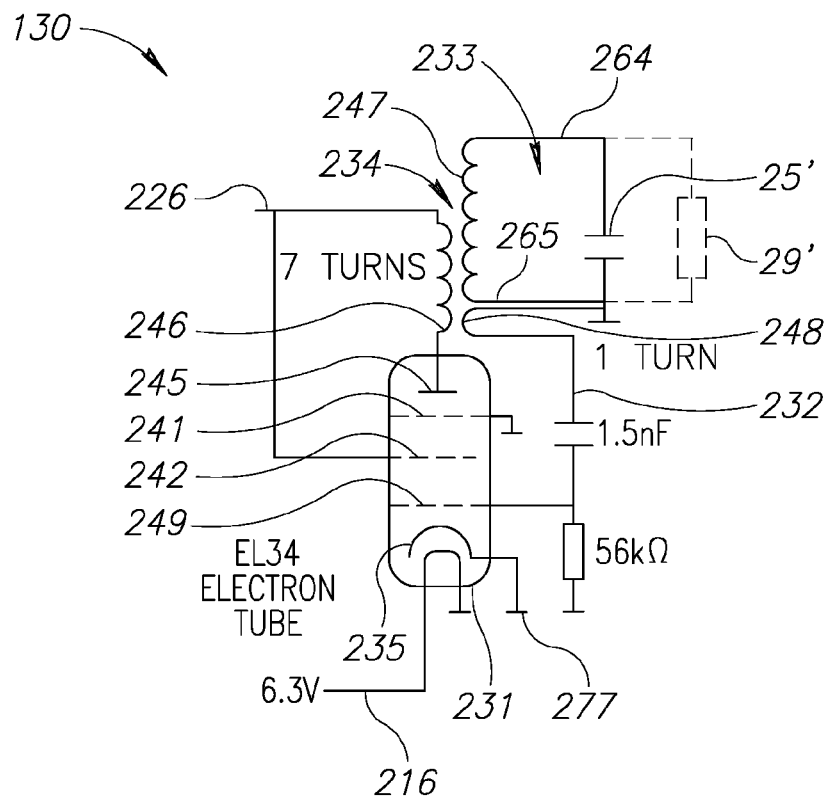

As indicated above, the plasma generating system described herein is configured for operation with high-frequency low voltage electric pulses. In this connection, reference is made to FIGS. 2A to 2F schematically illustrating an exemplary configuration of a power supply unit 22 and transmission channel 25 suitable for use on the plasma generating system 10. FIG. 2A exemplifies a schematic configuration of the power supply unit 22 and the transmission channel 25; FIG. 2B exemplifies power filtering and isolation circuit; FIG. 2C exemplifies RF power controller circuit; FIG. 2D exemplifies RF generator resonance circuit; FIG. 2E illustrates a general configuration of the power supply unit; and FIG. 2F exemplifies a configuration of the plasma generating unit 28.

FIG. 2A schematically illustrates an exemplary configuration of the power supply unit 22 in a way of block diagram 140. As shown, the power supply unit 22 is connected to the plasma generating unit 28 through electricity transmission channel 25 extending along the elongated member 26. In this example, the power supply unit 22 is formed by three main sections: power filtering and isolation circuit 110; RF power controller 120 configured for controlling and determining pulse sequence (e.g. voltage and duty cycle); and the RF generator section 130 (resonance circuit).

The different sections of the power supply unit are described in more details below, however it should be noted that according to the present technique, the electricity transmission channel 25, and in some configurations also the electrodes of the plasma generating unit 28, are part of the resonance circuit 130. More specifically, impedance, and specifically capacitance and inductance, of the transmission channel and the electrodes in considered as part of the impedance of the resonance circuit 130 and thus determined its resonance frequency.

FIG. 2B illustrates schematically an example of power filtering and isolation section 110 suitable for use on the power supply unit 22 according to the present technique. It should be noted that the filtering circuit may be used for a system 10 configured to be connected to an unfiltered power grid. However, if the system 10 is configured to be operated by batteries or connected to a stable grid, the filtering circuit 110 may be omitted.

Generally, the power filtering and isolation section/circuit 110 receives AC main electrical power at input 210. An input fuse 211 may be used for protection and a main switch 212 is generally used to enable turning on and off the power. The input power is transmitted to AC filtration unit 213 that includes coils/inductors and capacitors. The circuit 213 provides isolation between the input power lines and the downstream circuits of the power supply unit. This prevents leakage of RF signals generated within the system, as well as filters out noise and spikes that may be present on the power lines.

In some configurations, the filtering circuit section 110 may include a transformer unit 214. The transformer unit 214 may provide one or more of the following: complete or partial isolation of the power supply unit from the power grid, this is commonly used in medical electronic equipment which may come in contact with a patient; changing the AC voltage 215 provided to the power supply unit 22 to a desired level, for example to adopt the system to be used with input AC power of 110V as well as 220V, or any other level; and providing low voltage power (e.g. at about 6.3 V) 216 for heating the filament of the vacuum tube, which may be used in the RF generator resonance circuit 130. The power 216 for heating the tube may be AC or DC as the case may be.

Thus, filtered power 215 may be transmitted to the power control circuit 120. The RF power control circuit 120 is exemplified in FIG. 2C. The control circuit 120 may typically include a variable transformer 221 configured to controllably converts the AC voltage 215 to desired voltage level 222. The controlled voltage 222 may be provided to a dimmer 223 configured for converting the sinusoidal shape of controlled voltage 222 to a train of positive and negative pulses having desirably selected pulse width 229. The pulse series passes through a rectifier unit 224, which typically includes diode 225 configured to rectify the train of positive and negative pulses 229 and generate a train of positive pulses 226. The peak voltage of the pulse train is determined and controlled by the variable transformer 221 while the pulse width is controlled by the dimmer 223.

It should be noted that in this example, the repetition rate of pulse train 226 is determined by the frequency of the main power line 210. However this repetition rate may be varied using a frequency modulation circuit as generally known in the art. Generally the system 10 may be configured to utilize repetition rate between 100 Hz and 600 Hz.

It should also be noted that in configurations where the system 10 is operated by one or more batteries, and is not connected to the grid, filtering circuit 110 and power control circuit 120 may be omitted and replaced by controlled high voltage DC to DC power supply generating the output DC power 226 and a low voltage DC to DC power supply generating the tube heating voltage 216. Voltage of output DC power 226, its pulse width and repetition rate may all be controlled by the controlled high voltage DC to DC power supply.

FIG. 2D schematically illustrates an example of the RF generator circuit 130. The RF generator section 130 generally includes an amplifying element 231, e.g. a vacuum tube EL34 231 is shown in the figure, a step-up RF transformer 234, positive feedback 232 and a resonant circuit 233 configure generating high frequency pulses with desired voltage needed to ignite the plasma at the plasma generating unit. It should be noted that generally any type of amplifying element 231 may be used, for example, the amplifying element may be a vacuum tube or transistor or any other type of amplifying element. However, to facilitate understanding the following is described in the context to vacuum tube EL34 and should be interpreted broadly.

The cathode 235 of tube 231 is typically to be heated by low voltage 216 connected to its heating filament. Suppressor 241 grid and screen grid 242 are connected to the ground 277 and to output DC power 226 respectively.

The anode 245 of the tube 231 is connected to the primary coil/inductor 246 of the step-up RF transformer 234. The primary coil 246 may be configured with relatively low number of turns, for example only 7 turns. In some configurations, step-up RF transformer 234 may be core based or a coreless transformer.

Primary coil 246 is configured to be in inductive coupling connection with first 247 and second 248 secondary coils. The first secondary coil 247 is generally configured with higher number of turns than the primary coil 246 and is a part of a resonance RLC circuit 233. The resonance circuit 233 has effective capacitance 25' and effective resistance 29', both are determined in accordance with resistance and capacitance of the electricity transmission channel and the plasma generating unit as described above. Typically, inductance of the transmission channel is also considered in determined effective inductance of the circuit 233, this is not specifically shown in order to facilitate understanding of the first secondary coil 247. It should also be noted that in some configurations, additional capacitor, resistor and/or inductor may be used in resonance circuit 233 to provide desired frequency and performance.

The second secondary coil 248 of step-up RF transformer 234 is configured with lower number of turns than the primary coil 246 and is typically used to provide signals to the positive feedback route 232 connected to control grid 249 of the vacuum tube 231. For example, the second secondary coil 248 may be configured with one or two turns only.

According to some configurations, the RF generator circuit 130 is configured to generate electric pulses based on carrier RF frequency such that the RF frequency is tuned in with resonant frequency of resonance circuit 233. This provides an advantageous efficiency in providing high power to the plasma generating unit. Further, changes in the transmission channel and/or plasma generating unit may vary the effective impedance of the resonance circuit 233, however, the RF generator 130 aligns with the changed resonant frequency, requiring almost no interaction from an operator.

Figure 2F:
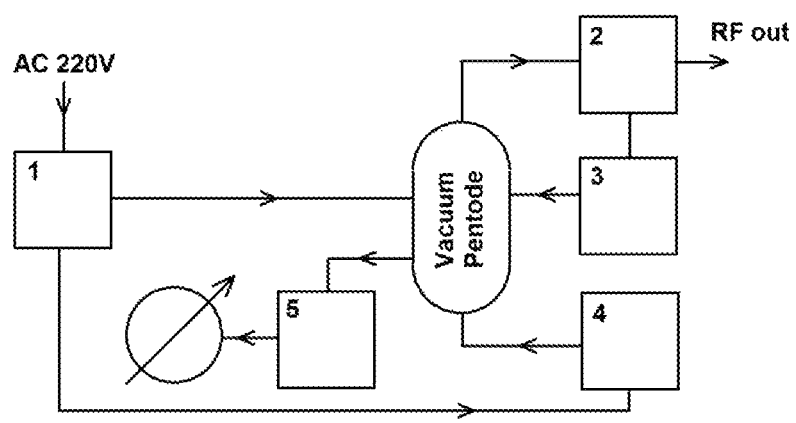

An exemplary configuration of the plasma generating unit 28 is illustrated in FIG. 2F. As described above, the plasma generating unit 28 is configured to be mounted at the distal end of probe 26 and operated by gas and electric pulses provided by the gas and electricity transmission channels 24 and 25. The electricity transmission channel 25 is preferably a coaxial cable and is configured such that inner 264 and exterior 265 conductors thereof are respectively connected to annular plasma electrodes 261 and 262.

The gas input is provided to gas tube 267 through the gas transmission channel 24. The input gas flows along the tube 267 to undergo discharge while being between the annular electrodes 261 and 262. In this exemplary configuration, the annular electrodes 261 and 262 are external with respect to a dielectric tube 269.

It should be noted that generally the gas tube 267 and coaxial cable 25 of the transmission channel (and the probe 26 itself) may be flexible. It should also be noted that the electricity transmission channel 25 and gas transmission channel (gas tube 267) are exemplified herein in a side-by-side fashion. However, coaxial cable 25 may be threaded inside gas tube 267. Additionally, in some configurations the plasma generating unit is covered by cover layer 270 for protection and aesthetics. In case the transmission channels are threaded together, the protection cover 270 may be used only on the plasma generating unit 28 head and not along the entire probe 26. The cover 270 is preferably electrically insulating, thereby assisting in eliminating the risk of electrical short circuit with the surrounding tissue.

Additionally, as indicated above, the external conductor, shield 265 of the coaxial cable 25 may be grounded and held at the same electrical potential as the treated tissue. This reduces the risk of electrocution as the tissue is in touch with conductor held at similar potential. Further, in some configurations, the corresponding electrode 262 of the plasma generating unit 28 is external to dielectric tube 269. This is while the inner conductor 264, carrying the electric signals, is connected to central may be placed inside dielectric tube 269. In this case, cover 270 may be used but not needed.

FIG. 2F is a general illustration of the power supply unit 22. As shown, the power supply unit includes a power source 1. The power source provides power to a resonance circuit 2 that is connected to a positive feedback 3 in connection with an amplifying element (e.g. tube). A control interface 4 is provided for selectively controlling repetition rate and pulse duration. The unit 22 may also include a measurement circuit 5 configured for monitoring operation of the system.

Reference is made to FIGS. 3A to 3D, illustrating a plasma generating unit configured according to the present technique and its connection to the elongated member (probe) 26.

Figure 3A:
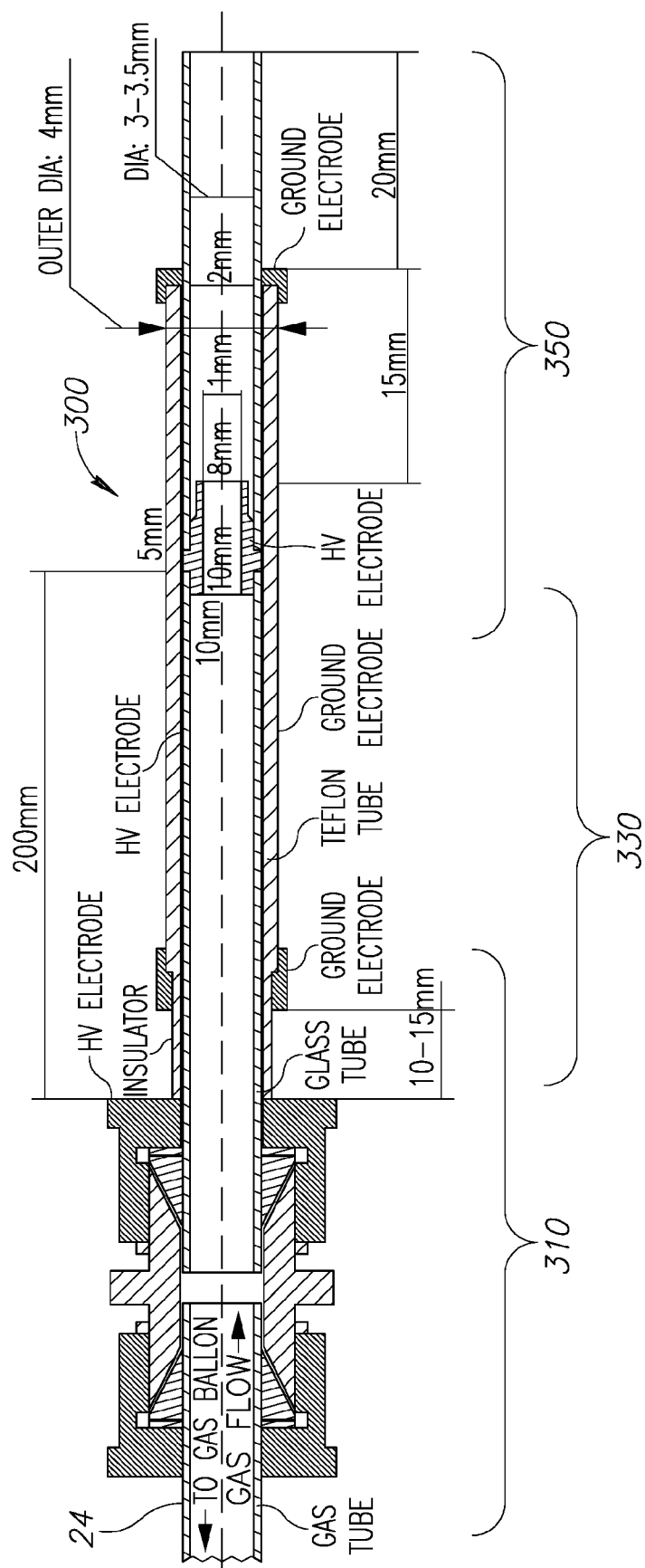
FIGS. 3A to 3D exemplify a configuration of the elongated member/probe and plasma generating unit according to some embodiments of the invention.

FIG. 3A exemplifies an illustration of a cross section of the probe and the plasma generating unit according to some embodiments of the present invention. The distal end 300 of the probe and the plasma generating unit may be schematically divided to three sections: connector section 310, tube section 330; and plasma gun section 350 (plasma generating unit). The three sections are described below with reference to FIGS. 3B to 3D in more details. However it should be noted that the materials and dimensions given here are presented as non-limiting demonstration.

Figure 3B:
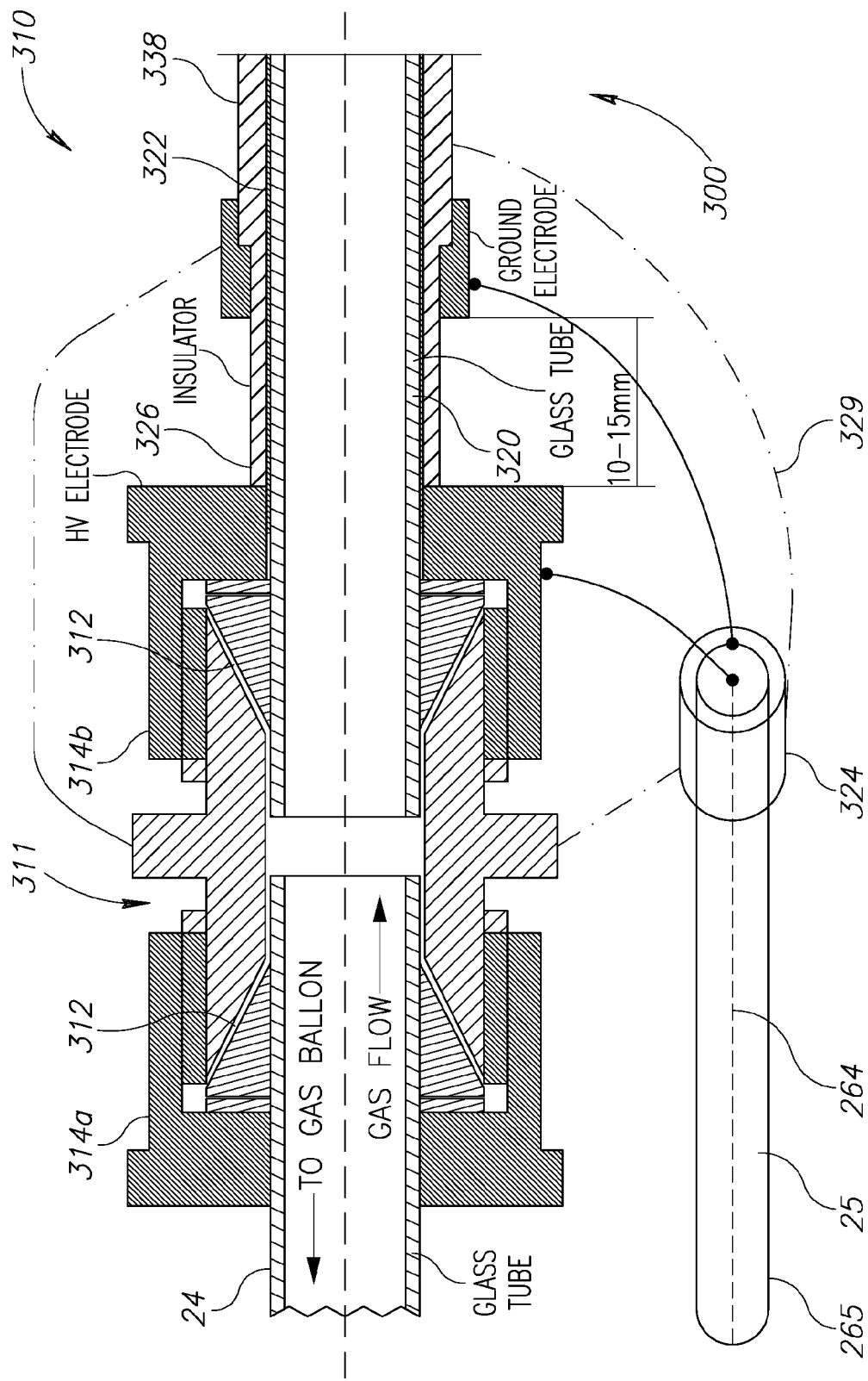

FIG. 3B exemplifies a cross section of the connector section 310 connecting the elongated member carrying the electricity transmission channel and gas transmission channel to the distal end thereof and to the plasma generation unit. The gas pipe (also termed gas tube or gas transmission unit) 24 is inserted from the left hand side of gas connector 311. The connector is configured with gasket 312 and tightening nut 314a to prevent gas leaks. As indicated above, the gas pipe 24 is preferably flexible such that probe 300 may be moved about.

On the other side of the connector, a glass gas tube 320 is inserted and configured to transmit the gas to the plasma gun. Additional tightening nut 314b may be provided at the distal (gas tube 320) side. The tightening nut 314b may be metallic to allow electrical contact with inner conductive layer 322 of the plasma gun, deposited on the outer surface of glass tube 320, configured to provide electric connection tot eh electrodes of the plasma gun as shown in the following figures in more details. For example, the inner conductive layer 322 is electrically connected to inner/central conductor 264 of the electricity transmission channel 25, e.g. through nut 314b, or through other connections as the case may be. Generally, the conductive layer 322 is covered by an insulating layer 326. The insulating layer 326 may be made of Teflon or any other suitable material.

The external conductor 265 of the electricity transmission channel is connected to a ground layer 338 that is configured to cover insulator layer 326. The ground layer 338 is further connected to ground electrode 351 (as shown in FIG. 3D). This connection may be done via an optional connector 324. In some configurations, the entire connector section 310 may be covered with cover 329 such that no high-voltage components are exposed.

It should be noted that the connector, as well as the probe and the plasma generating unit, is configured such that the outer layer thereof is grounded and provides shielding to the surrounding. This is to prevent any electrical hazard to the patient and thus allowing the system to be used on live biological tissue.

It should also be noted that the various conductors on the connector and the plasma generating unit may be configured as silver coating on glass tube (e.g. tube 320) and insolating layer 326 respectively.

Figure 3C:
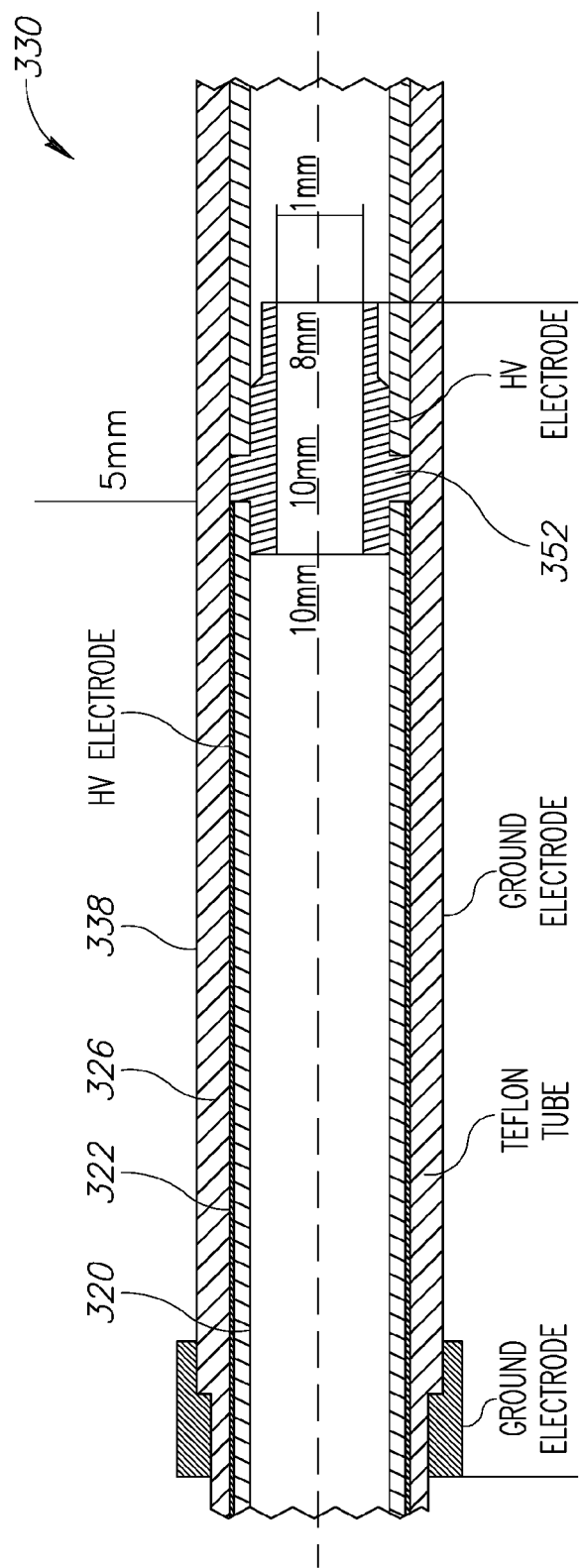
Figure 3D:
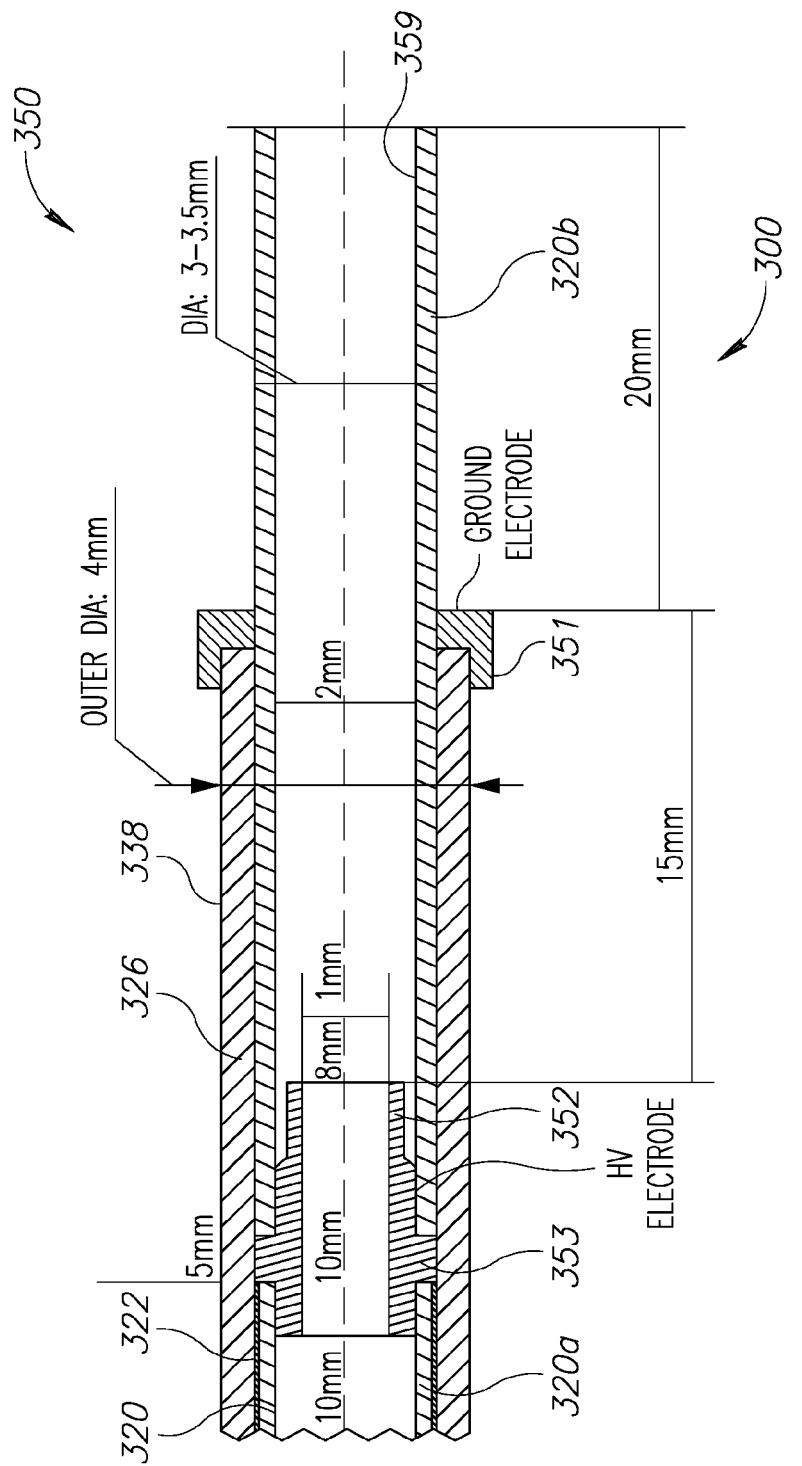

FIG. 3C schematically illustrates a cross section of the tube section of the plasma generating unit, extending distally to the connector section 310. Tube section 330 may be as long as the application requires. Along the tube section 330, the inner conductive layer 322 is generally separated from the ground layer 238 by the thin insulator layer 326. Thus, the inner conductive layer 322 and the ground layer 238 form a coaxial transmission channel (and a capacitor) and contribute to the total effective capacitance 25'. This capacitance thus depends on the length of tube section 330 as well as other parameters such as the diameter of the inner conductive layer 322 and the ground layer 238, and the dielectric coefficient of the insulator layer 326. Also shown in this figure is the inner electrode 352 of the plasma generating unit, connected to the inner conductive layer 322.

FIG. 3D schematically illustrates a cross section of the plasma gun section 350 according to some embodiments of the invention. Plasma gun section 350 is mountable at the distal end of the probe 300. The plasma gun 350 is typically based on dielectric barrier discharge scheme by transferring gas between two electrodes with high potential difference between them as described above. An inner electrode 352 is internal to glass tube 320 and electrically connected to the inner conductive layer 322 via holes in the glass tube. Alternatively glass tube 320 is made of two parts 320a and 320b held together by insulation layer 326 and configure to provide electric contact to the electrode 352. The inner electrode 352 thus receives electric pulses generated by the power supply unit 22 described above.

A ground electrode 351 is positioned distally to the inner (High Voltage) electrode 352, on the outer surface of glass tube 320. The ground electrode is preferably located just beyond the end of insulator layer 326 as close as possible to exit aperture of the plasma generating unit.

As indicated above, application of varying electric field (at high frequency) with high potential difference, between the electrodes 352 and 351 in combination with passage of gas through the tube provides for generating plasma at temperature determined by voltage (potential difference) and carrier frequency of the pulses. The cold plasma exits the opening 359 of the glass tube 320 directed to treat the target tis sue.

It should be noted that the probe and plasma generating unit as described above may be configured to be of very narrow cross section, i.e. very thin. For example, the elongated member and the plasma generating unit at the distal end thereof may have an outer diameter of about 4 mm. The thin construction allows it to be used in narrow, yet deep cavities, and make it suitable for endoscopic applications. It should also be noted that although the cross section of the tube and plasma generating unit exemplified herein is substantially circular, the cross section may be of any arbitrary shape. For example, the system may utilize rectangular tube or have the form of thin ribbon type plasma flow. Alternatively, the tube may be configured with multi-bores to produce several plasma flows, or any other cross sections. Optionally different parts of the tube may have different cross section or made of different materials.

Thus, the present invention provides a system and a technique for generating cold plasma utilizing high-frequency pulses. The system is suitable for use on living organisms and is configured to eliminate, or at least significantly reduce any risk of electricity damage to surrounding living tissue. In order to test the effectiveness of treatment using the cold plasma generating system described above, the inventors have conducted a series of in-vitro and in-vivo treatment sessions as follows.

Figure 4A:
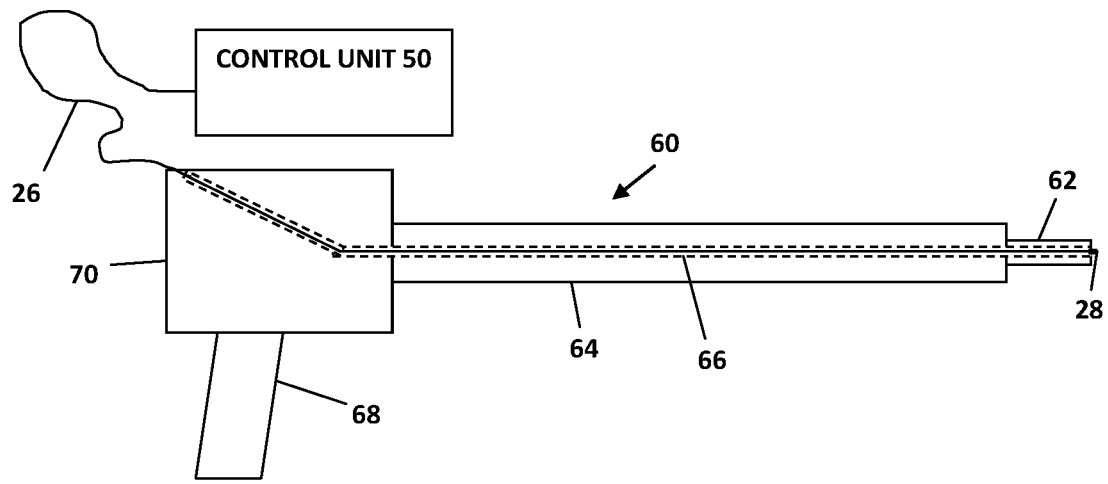
FIGS. 4A to 4B exemplify two configurations of the probe according to some embodiments of the invention as add-on for endoscope system (FIG. 4A) or as rigid standalone catheter (FIG. 4B)
Figure 4B:
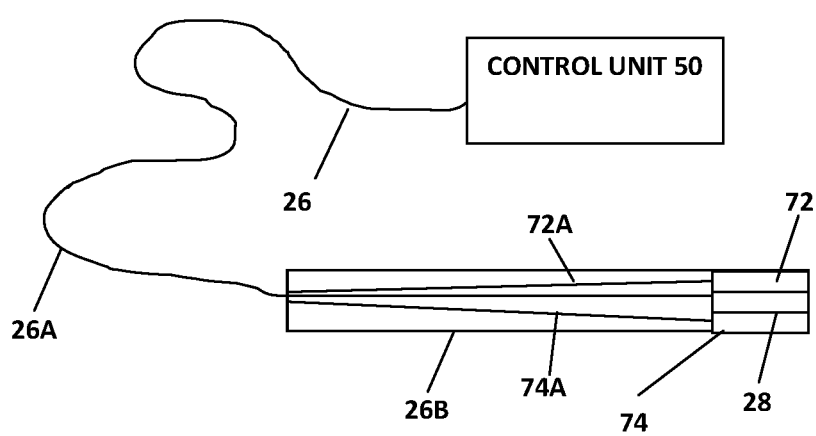

In this connection, reference is made to FIGS. 4A and 4B exemplifying two configurations of the elongated member/probe 26 of the plasma generating system for use in in-cavity plasma application. FIG. 4A exemplifies the probe 26 being directed through a working channel of an existing endoscope and FIG. 4B exemplifies a rigid catheter configuration of a distal portion of the probe 26 enabling stand-alone configuration.

FIG. 4A schematically illustrates an endoscope unit 60 having a control section 70, catheter section 64 and operations distal end 62. Typically the endoscope may also include a handle 68 to allow a used easy grab. The endoscope is typically equipped with lighting unit and optical sensor that are not specifically shown, as well as various additional sensors or working elements as the case may be. Additionally, the endoscope may include a working channel 66 configured as a hollow channel along the catheter, allowing suitable additional components to be inserted there through and allow additional functionalities that may be required in certain operations/uses.

As described above, the elongated member 26 of the presently described plasma generating system 10 may be configured as an elongated narrow catheter. The probe 26 and the plasma generating unit 28 thereof may be configured to be desirably inserted into the working channel to thereby enable application of plasma at desired location to be part of the medical operation.

Typically such probe configuration may be more suitable for use in surgically mad cavities as well as in narrow and deep cavities such as in the gastro-intestinal system, vascular system etc. or generally wherever the use of endoscope is desired or needed.

Alternatively or additionally, FIG. 4B illustrates a stand-alone configuration of the elongated member 26 of the plasma generating system 10. In this configuration the elongated member 26 has a flexible proximal portion 26A and a relatively rigid distal portion 26B extending to the distal end carrying the plasma generating unit 28. This rigid configuration allows an operator to direct the generated plasma to a desired location manually or by an automated robotic arm. This configuration is more suitable for use in relatively open cavities such as the mouth. However such rigid configuration may also be advantageous in surgically opened cavities such as in open surgery of the abdomen etc.

Also exemplified in FIG. 4B is one or more additional sensors located at the distal end of the probe 26. In the figure two such additional sensors 72 and 74 are exemplified, including cable connections 72A and 74A extending to the control box 50. Such additional one or more sensors may include for example one or more of the following: temperature sensor (e.g. thermocouple type or any other thermal sensor), a spectrometry sensor (e.g. photo-spectrometer), electric and or magnetic field sensors or any other type of sensor.

For example, the thermal sensor and/or spectrometry sensor may be used to characterize properties of the generated plasma such as temperature, ionic composition etc. the use of such additional one or more sensors may provide feedback information to an operator and or be used in a feedback loop of the system to prevent over increase in plasma temperature and thus reduce repetition rate of peak voltage. Additionally, data about ionic composition may provide indication of plasma efficiency as existence on ions that were not introduced in the input gas composition may indicate that the electrons and/or ions of the plasma interacted with nearby biological tissue and generated secondary ions.

Figure 5A:
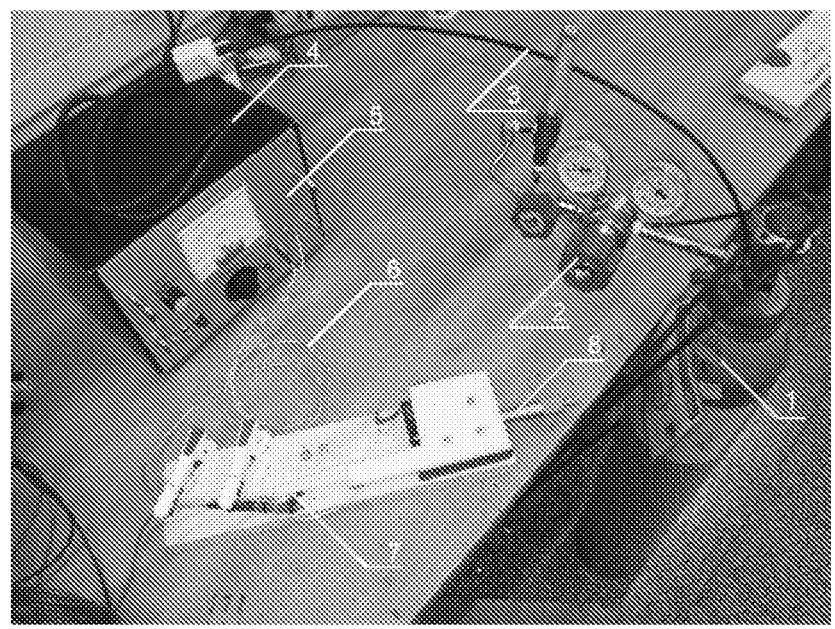
FIGS. 5A to 5F show experimental plasma generating system and results of plasma measurements performed.

In order to characterize the plasma generated according to the present technique, as well as its efficiency in treatment of biological tissue, the inventors have constructed the system as illustrated in FIG. 5A. Further the inventors have performed several measurements exemplified in FIGS. 5B to 5F.

The general construction of the experimental setup is shown in FIG. 5A includes gas-network system including of a cylinder 1, filled with Penning mixture gas, i.e. 98.5% Ne+1.5% Ar (however any other gas mixture may be used). The cylinder 1 is connected to a flow meter 3 via a pressure reducer 2. The reducer 2 output is directly connected to gas input of the plasma gun 7. The system also includes an RF generator 5 connected by power cable 4 to standard electrical grid providing 220V 50\60 Hz AC power. The RF generator 5 and the plasma gun 7 are connected to each other by low-loss coaxial flexible cable 6. The plasma gun 7 is held by support 8 to simplify the experimental process, generally the plasma gun is mounted on a distal end of probe as described above. In this example, the support 8 is used for holding plasma target with measuring tool.

The RF generator 5 generates RF pulses with required voltage, repetition rate, pulse duration and desired duty cycle as described above. In this exemplary configuration, the RF generator allows varying these parameters in ranges of: voltage between 750V and 1150V; pulse duration between 450 µs and 800 µs, pulse repetition rate between 150 Hz and 660 Hz. All pulses were transmitted over carrier frequency of 1 MHz controlled by the resonance circuit of the RF generator 5 (power supply unit).

This configures may be used with different types of plasma-guns (plasma generating unit) and was designed and tested with the plasma guns exemplified and listed in the following table 1. All these plasma guns generate stable cold plasma plumes with different lengths and diameters as described in the table. The inventors have found that plasma gun operation may be characterized by two different modes resulting in different plasma plume parameters. A first mode, so-called free-blowing regime ("Current I") is achieved when the plasma plume is not in contact with the target and the second, more energetically target-contacting, regime ("Current II"). The below described measurements were carried out when the plasma gun was operated in Current II mode of operation. The power of the plasma spot is almost independent on the distance between the plasma gun output and the target, but it is strongly dependent on parameters of the RF pulse.

TABLE 1

List of plasma-guns

| Number of gun | Name | ID mm | OD mm | Outlet nozzle diam., mm | Width of the ring, mm | Length of inner steel contact, mm | Length of plasma gun, mm | Number of gun |
|---|---|---|---|---|---|---|---|---|
| 1 | Capillary CV6084Q (one stripe) | 0.60 | 0.84 | 0.84 | 4.00 | 11.00 | 53 | 1 |
| 2 | Capillary CV8010Q (two stripes) | 0.80 | 1.00 | 1.00 | 4.50 | 11.00 | 51 | 2 |
| 3 | Capillary CV1012Q (three stripes) | 1.00 | 1.20 | 1.20 | 0.09 | 11.00 | 53 | 3 |
| 4 | Small plasma gun | 1.15 | 2.10 | 2.10 | 0.09 | 0.00 | 45 | 4 |
| 5 | Middle plasma gun (SHORT) | 1.75 | 3.00 | 3.00 | 0.09 | 0.00 | 15 | 5 |
| 6 | Large plasma gun | 2.95 | 4.50 | 4.50 | 0.09 | 0.00 | 53 | 6 |
| 7 | Cone-like nozzle gun | 4.00 | 3.00 | 0.50 | 0.09 | 0.00 | 52 | 7 |

Figure 5B:
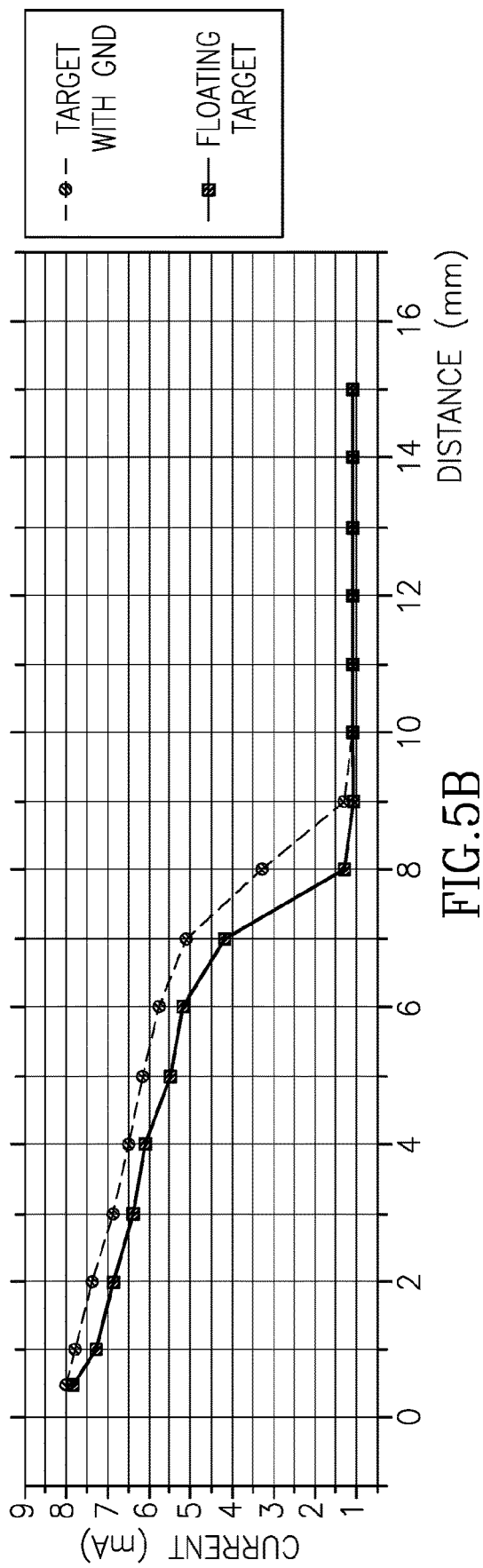
Figure 5C:
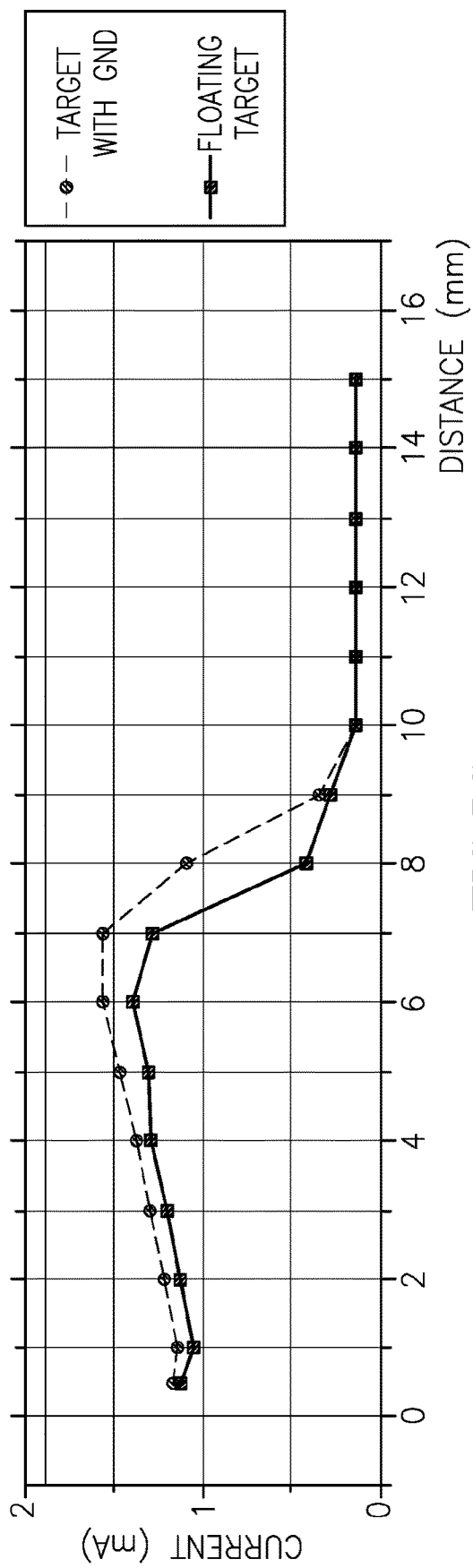

A copper plate of dimensions of 7 mm×15 mm×0.2 mm was used as a plasma target. The inventors have found the there is no noticeable difference in parameters of the power delivered to the plasma plume when the target is grounded via 10 kΩ resistor or electrically floating. FIGS. 5B and 5C show variation of the current through the plasma plume and the delivered power to the plasma plume as function of distance from the plasma gun opening and the target. These figures show measurements for targets grounded through 10 kΩ resistor and floating target. In this example plasma gun number 3 was used (Capillary CV1012Q (three stripes)) with gas flow rate of 0.5 L/min, peak voltage of 850V and repetition rate of 222 Hz. As shown the increase in the distance between zero and 8 mm leads to a decrease in the current but an increase in delivered power. This may indicate an increase in the plasma resistivity. Nevertheless, the change in the delivered power over the distance of about 7 mm (with error margins of 0.5 mm) seems not to be significant and may indicate that within this distance the delivered power does not change more than 30%. It should however be noted, and as seen in this figure, that at certain distance of the target, the plasma plume transfers from Current II mode to Current I mode. In this example at distances larger than 9 mm the plasma gun operation is characterized by Current I mode with almost 8 time less power delivered to the plasma plume while having almost no dependency on the distance of the target. These dependencies of RF current and power were obtained for all plasma guns developed and tested by the inventors and for the entire range of tested frequencies between 500 kHz and 4 MHz. Additionally, this did not seem to vary with changes in repetition rate and pulse duration. More specifically, low-power Current I mode was obtained at large distances and high-power Current II mode was realized at short distances.

Figure 5D:
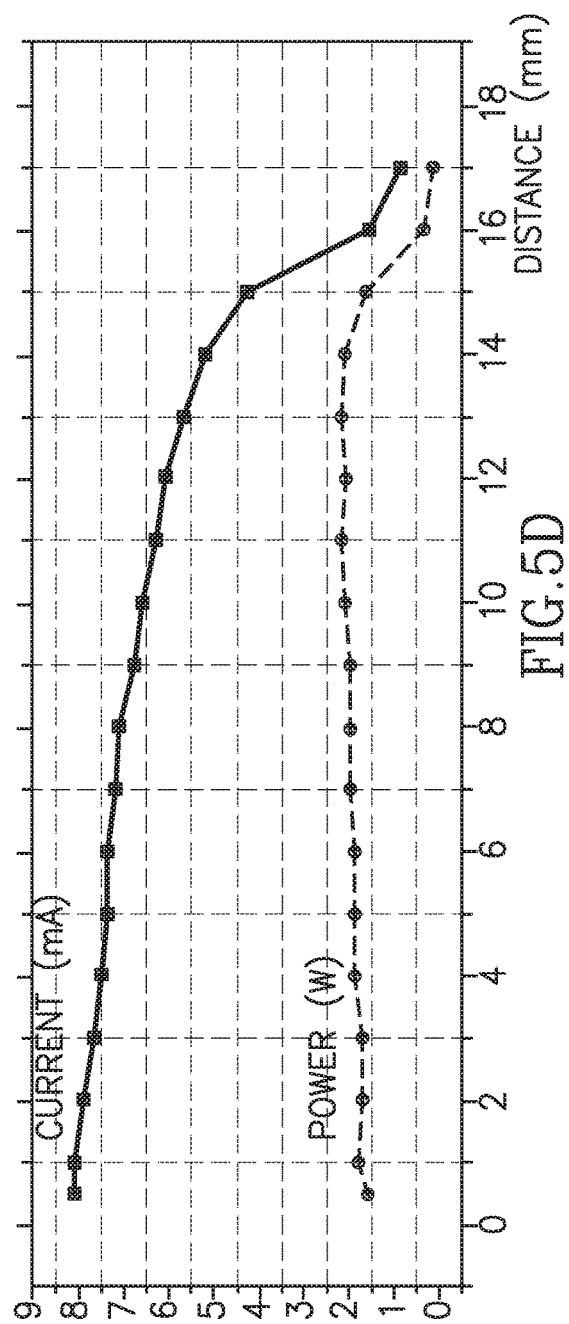

FIG. 5D shows current and RF power as function of distance of the target at higher gas flow rate of 2 L/min. As shows, an increase in gas flow rate may leads to an increase of the target distance while the plasma gun operates in Current II mode, i.e. plasma plume in contact with target. Similarly, the peak voltage used here is 850V with repetition rate of 222 Hz.

Figure 5E:
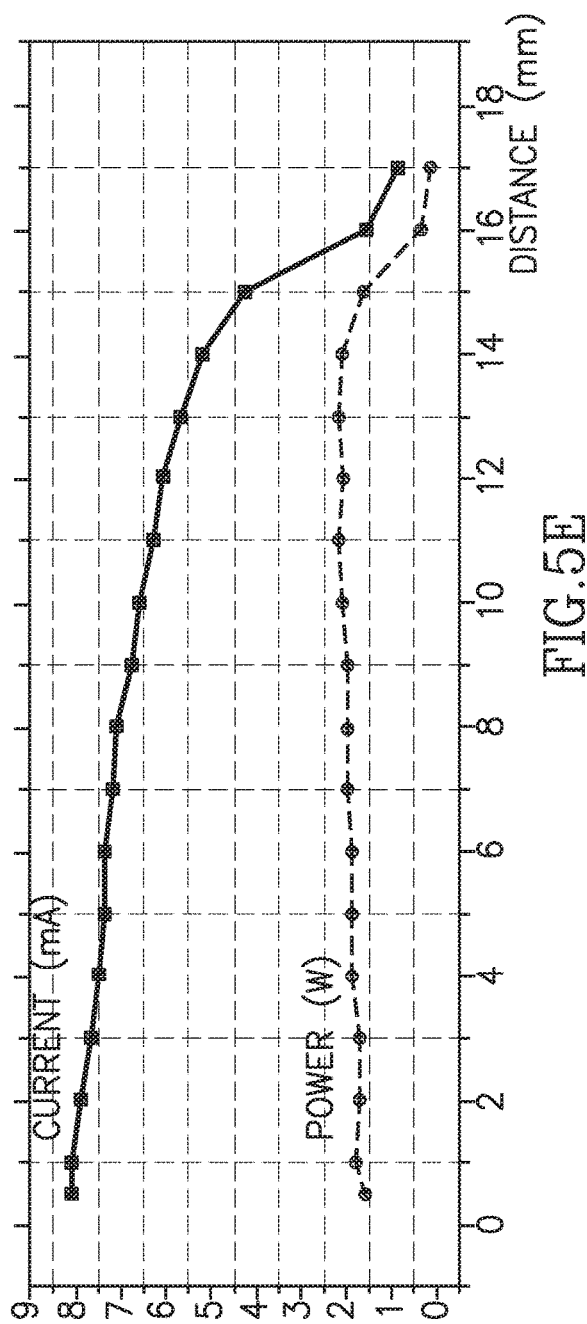

The inventors have found that a decrease in either one or both the RF pulse voltage to (e.g. to 750V) and gas flow rate (e.g. to 0.5 L/min) results in decrease of RF current through the plasma as well as in the RF power. However the peak voltage and the gas flow rate have different effect of the variation in current and power as a function of target distance. FIG. 5E shows plasma current and power as function of distance for peak voltage of 750V and gas flow rate of 0.5 L/min. In comparison to the above FIGS. 5B and 5C the current mode distance is similar. However as shown in FIG. 5D an increase in flow rate results in increase in the target distance supporting Current mode II. More specifically, the "length" when Current II regime exists, is reduced from 8 mm to 6.5 mm as compared to peak voltage of 850V.

This provides estimation on the power directed at the plasma plum as a function of peak voltage and gas flow rate. The RF average power may also be easily estimated as a product pulse power and the duty cycle, determined by the pulse duration and the repetition rate.

Figure 5F:
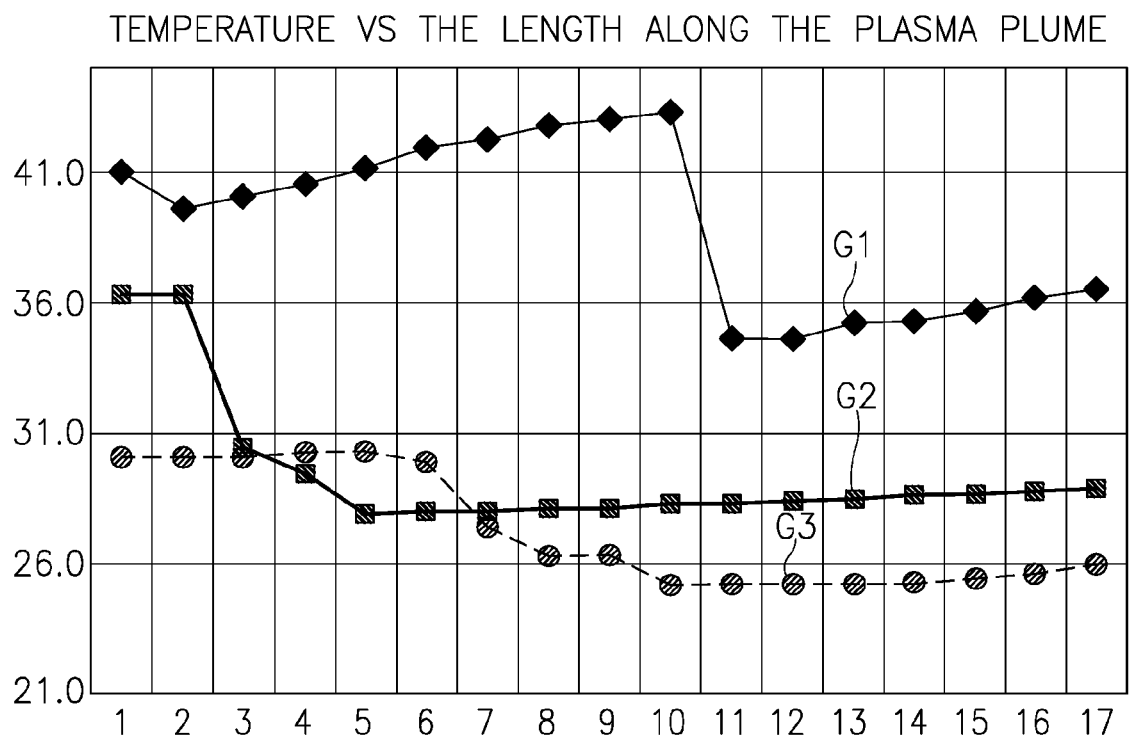

FIG. 5F shows temperature measurement of the generated plasma at different distances for flow rate of 1 L/min and 2 L/min and peak voltage of 750V and 1400V. More specifically, line G1 relates gas flow of 1 L/min and voltage of 1400V, line G2 relates to gas flow rate of 2 L/min and voltage of 750V and line G3 relates to gas flow rate of 2 L/min and voltage of 1400V. The temperature measurements were performed using plasma gun 3 (Capillary CV1012Q (three stripes)) described above and pulse repetition rate of 222 Hz and duration of 750 ms. The temperature measurement was done by Ar—Ga fiber-optical thermometer and the initial gas temperature=24.6° C.

As shown, higher flow rate or lower voltages decrease the plasma temperature. As also shown, the plasma temperature does not exceed 43° C. and can be maintained around 30° C., depending on power profile.

Figure 6A:
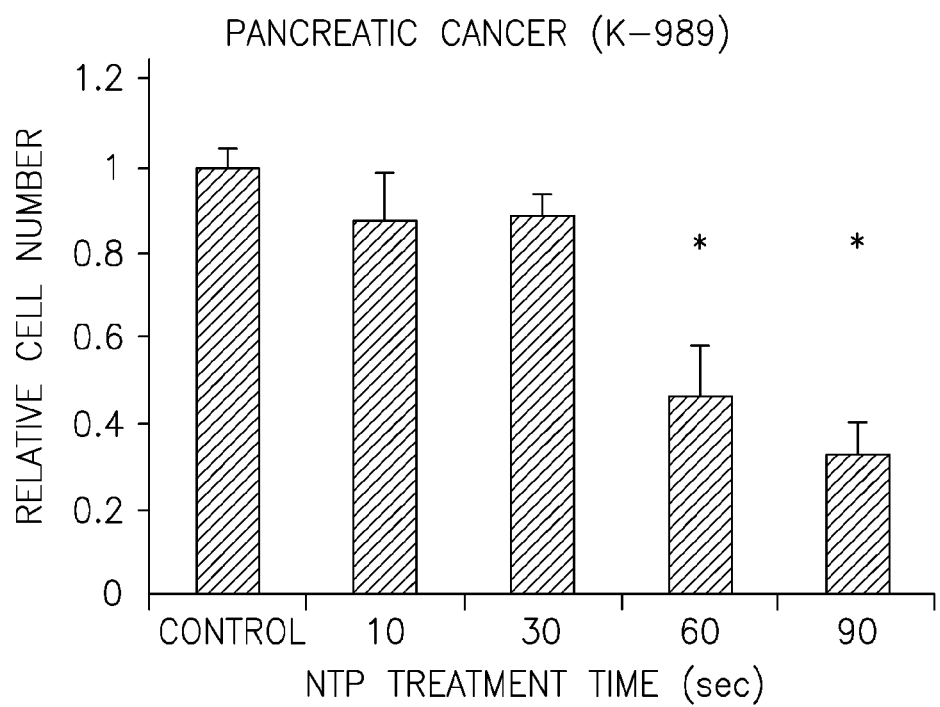
FIGS. 6A to 6F show in-vitro treatment of cancer cells using plasma according to some embodiments of the invention.
Figure 6B:
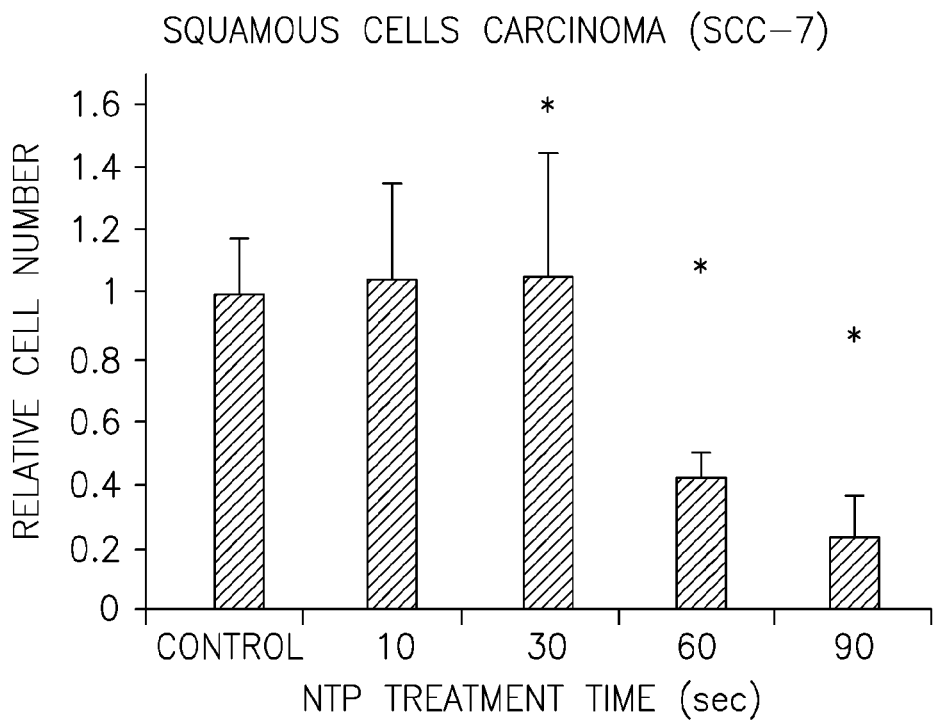
Figure 6C:
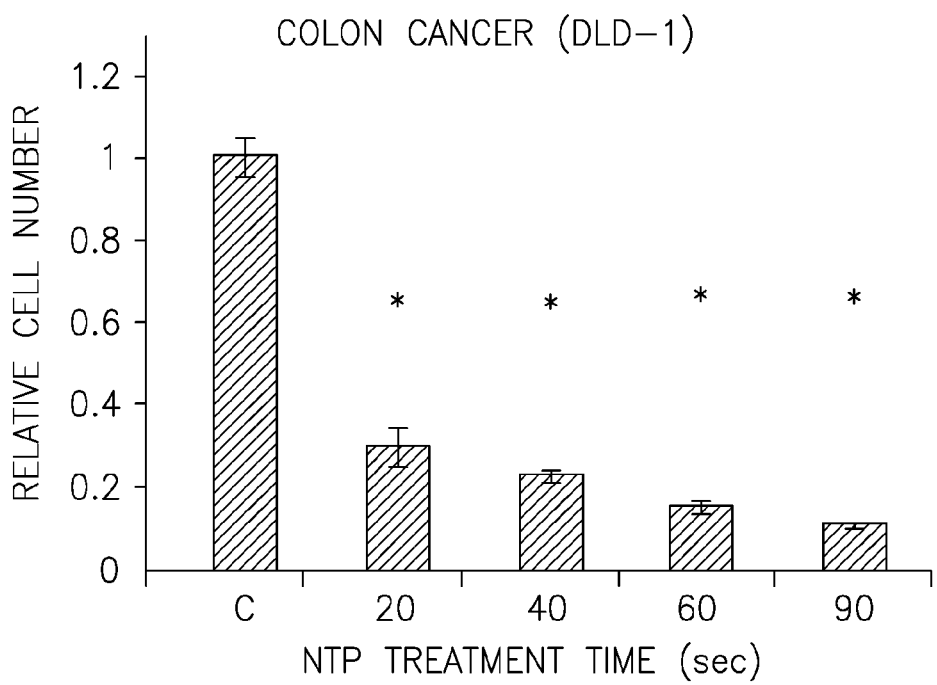
Figure 6D:
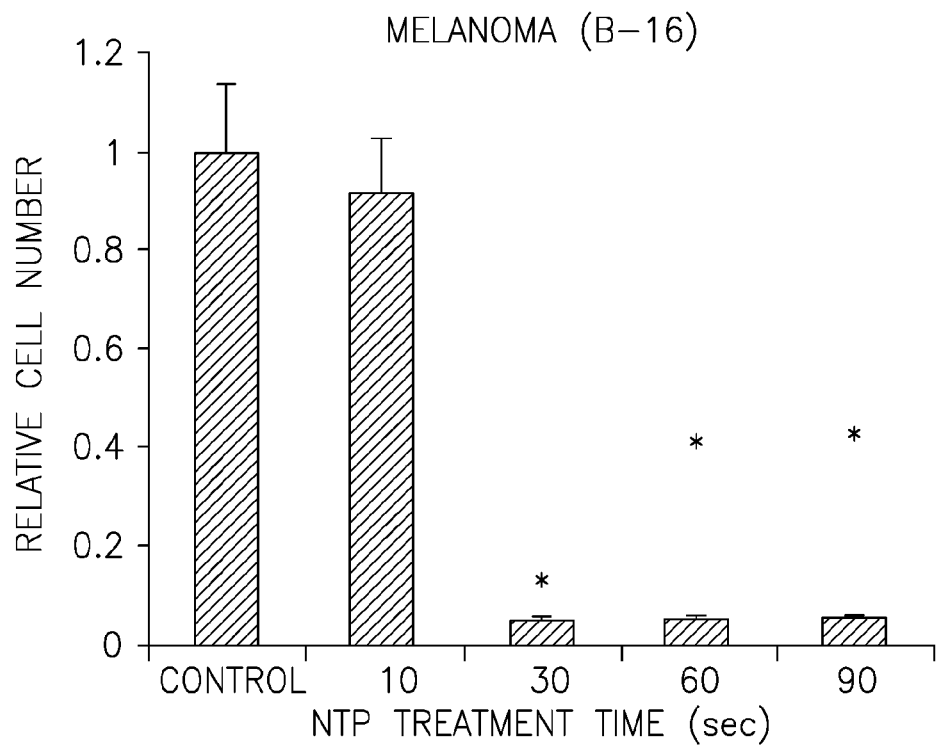
Figure 6E:
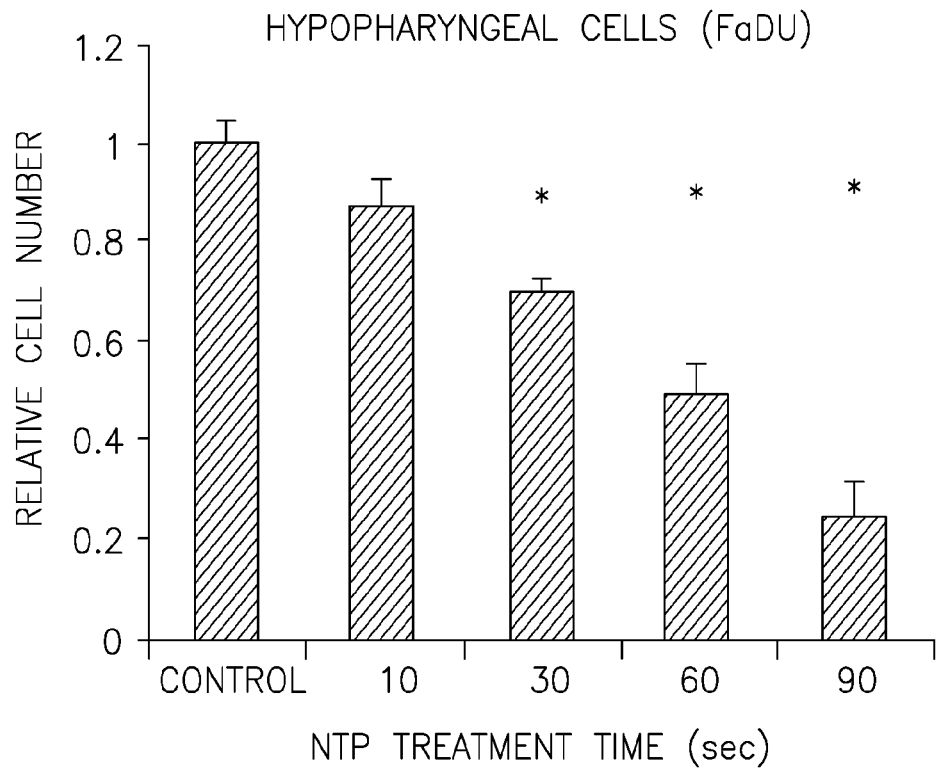
Figure 6F:
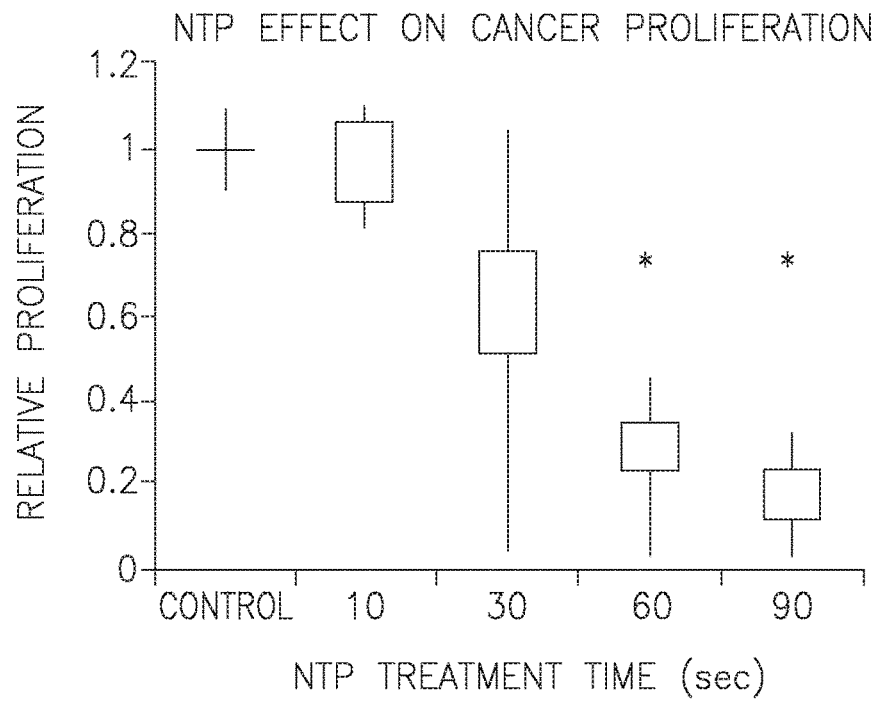

Reference is made to FIGS. 6A to 6F showing in-vitro experimental results comparing plasma efficiency in treatment of cancer cell of different type. FIG. 6A shows treatment result of Pancreatic cancer cells; FIG. 6B shows treatment results of Squamous-cell carcinoma cells; FIG. 6C shows treatment results of Colon cancer cells; FIG. 6D shows treatment results of Melanoma cells; and FIG. 6E shows treatment results of Hypopharyngeal cells. Additionally, FIG. 6F Summarizes response of all cancer cell lines to NTP therapy according to the present technique.

In each experiment, 100,000 cancer cells were treated with NTP for different time durations. As control group, cells were treated with gas only (having the electrical current turned off). 48 hours post treatment, an XTT assay (using (2,3-bis-(2-methoxy-4-nitro-5-sulfophenyl)-2H-tetrazolium-5-carboxanilide)) was performed to assess cell proliferation, providing data about relative cell number.

As shown, all cells responded to NTP treatment, and demonstrated 67% and more proliferation reduction at 90 seconds of treatment (p<0.05 for all cells). Pancreatic cancer (FIG. 6A) cells displayed the lowest proliferation reduction at 90 seconds (67.5% reduction) followed by Squamous cell carcinoma cells (FIG. 6B) showing 76.49% reduction. The Hypopharyngeal cells (FIG. 6E) showed 76.6% reduction, melanoma cells (FIG. 6D) showed 94.9% reduction. Colon Cancer cells, shown in FIG. 6C, were most sensitive to NTP treatment showing 97.50% reduction. As shown in FIG. 6F, on average, 60 seconds of NTP treatment causes significant reduction in proliferation, e.g. between 53-97% reduction relatively to control (p=0.0003) and 90 seconds of treatment resulted in 67.5-97.5% proliferation reduction relatively to control (p=4*$10^{-5}$).

Figure 7A:
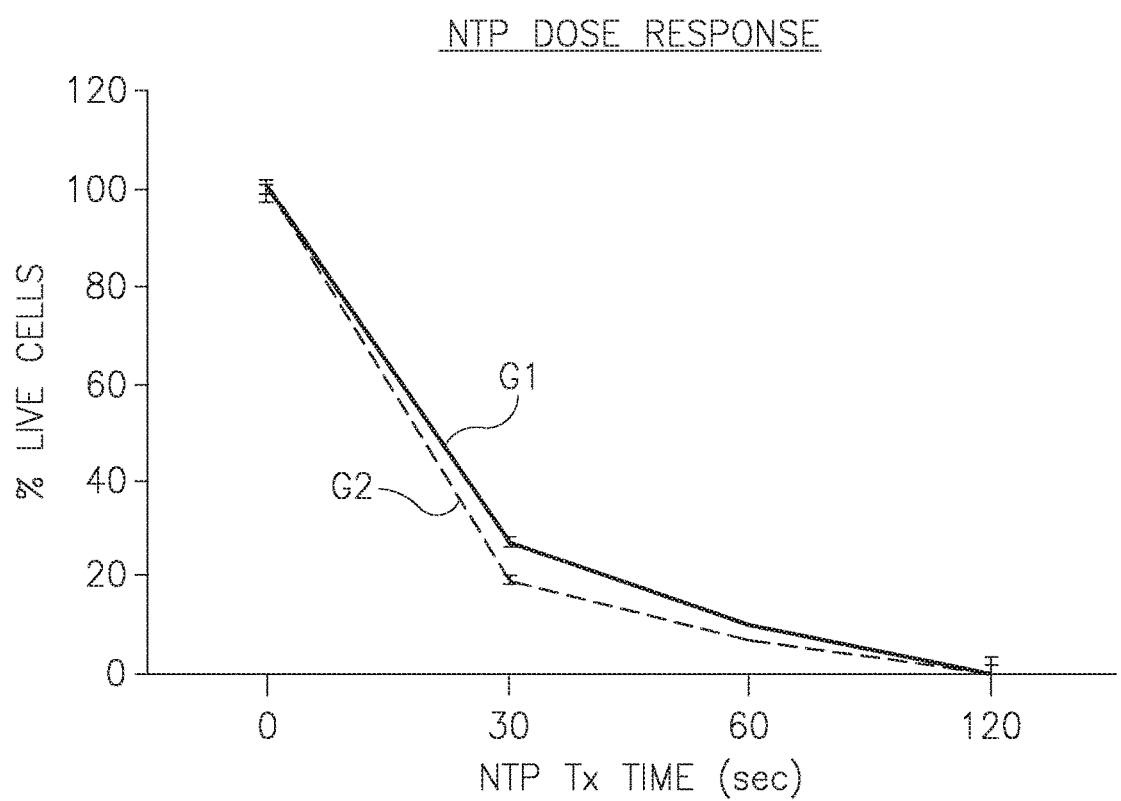
FIGS. 7A and 7B show additional results of in-vitro cold plasma treatment of cancer cells according to some embodiments of the invention.
Figure 7B:
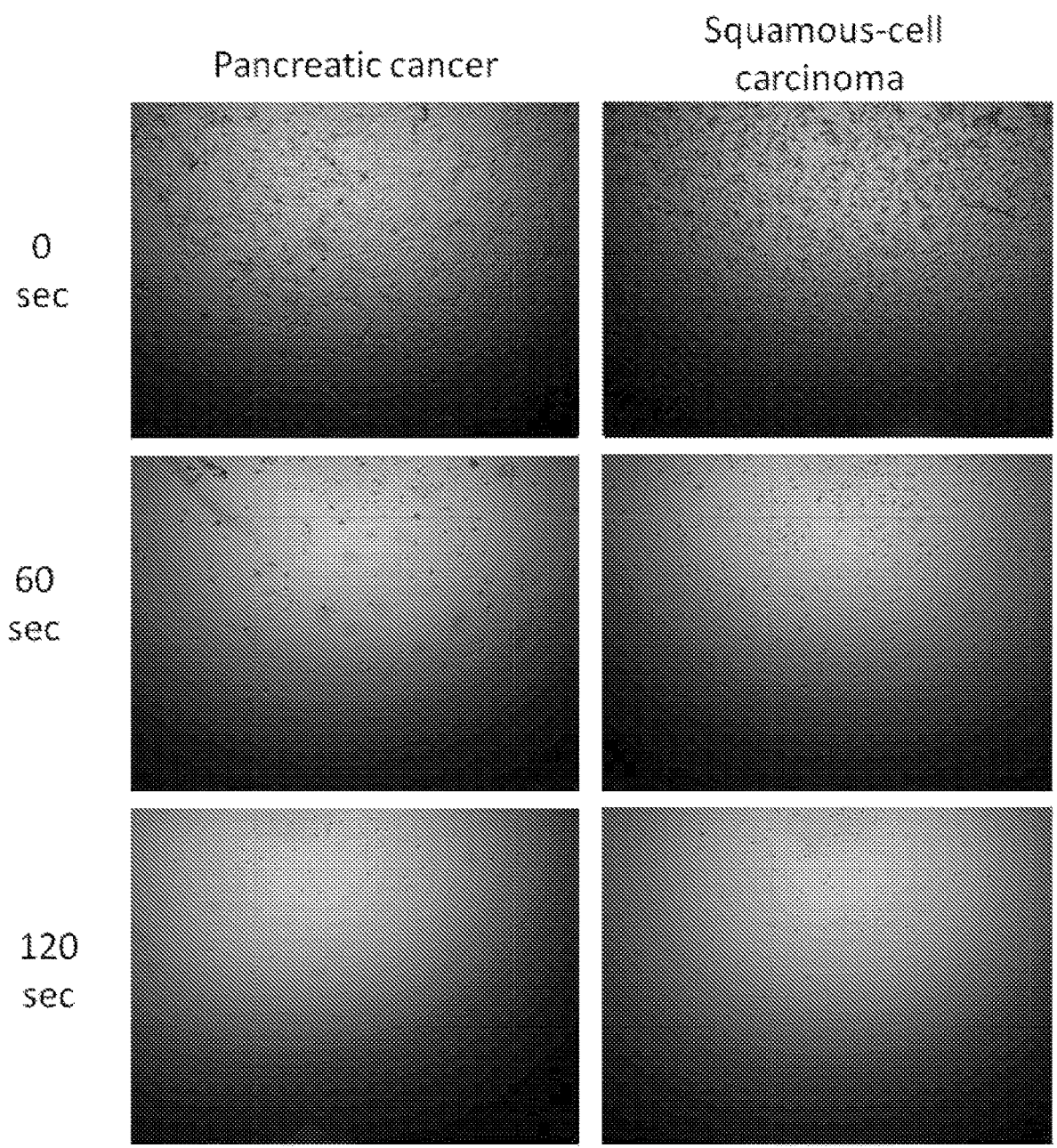

Reference is made to FIGS. 7A and 7B showing results of NTP application on Pancreatic cancer cells (K-989) and Squamous-cell carcinoma (SCC-7). FIGS. 7A and 7B show experimental results of NTP application on 100,000 cancer cells in medium volume of 100 μL for different time durations. FIG. 7A shows percentage of remaining live cells, were G1 line shows percentage of live Pancreatic cancer cells and G2 line shows percentage of live Squamous-cell carcinoma. FIG. 7B shows microscope images of the cells after exposure to NTP. Control cells were treated with gas only, while the power pulses were turned off. The plasma parameters in this experiment were as follows: The plasma gun model used is model 2 (Capillary CV-8010Q (two stripes)), located at 8 mm distance from the cells. The plasma was generated using 850V pulses with duty cycle of 750 ms and carrier frequency of 1 MHz. Additionally the experiment used variator position of 5 (152 Hz).

As shown, Pancreatic cancer (K-989) cells displayed 19.4%, 6.85% and 0% liveliness after 30, 60 and 120 seconds of NTP treatment respectively. SCC-7 cells showed 26.9%, 9.32% and 0.68% liveliness for similar treatment durations. All these numbers are relatively to the control untreated cells.

The microscope images of the cells at 0 seconds of treatment (Control), 60 seconds and 120 seconds are shown in FIG. 7B. These images confirm that for 120 seconds of NTP treatment, virtually all cells were killed by plasma treatment.

Figure 8A:
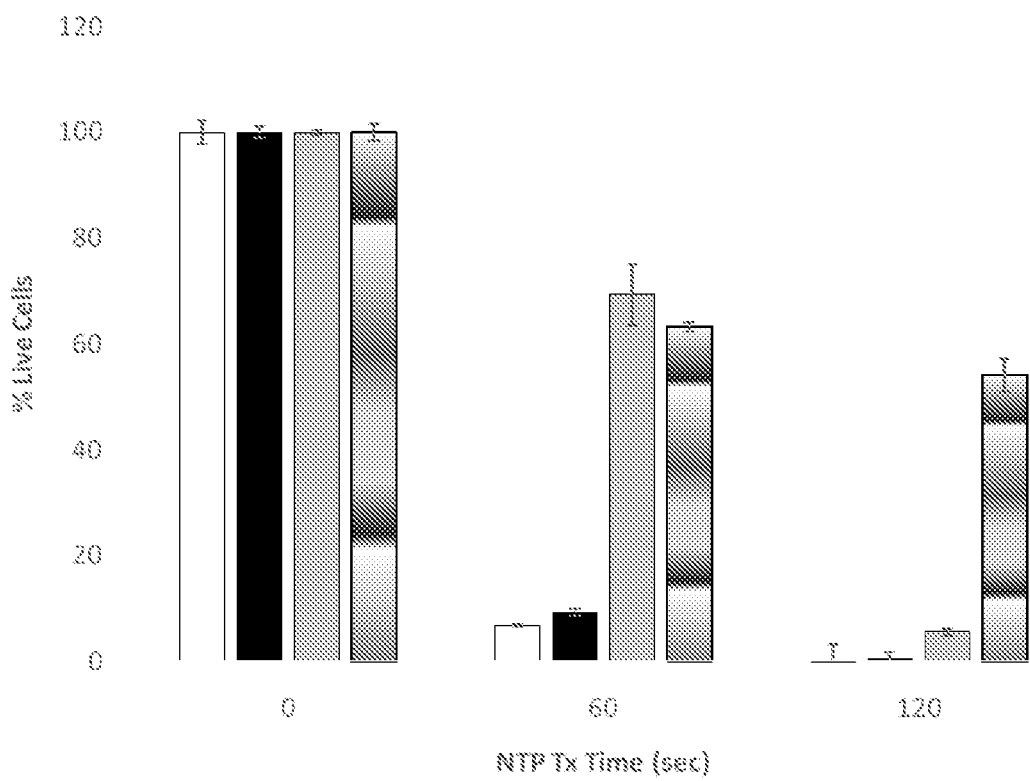
FIGS. 8A and 8B show over time results of cancer and control cells post cold plasma treatment according to some embodiments of the invention.
Figure 8B:
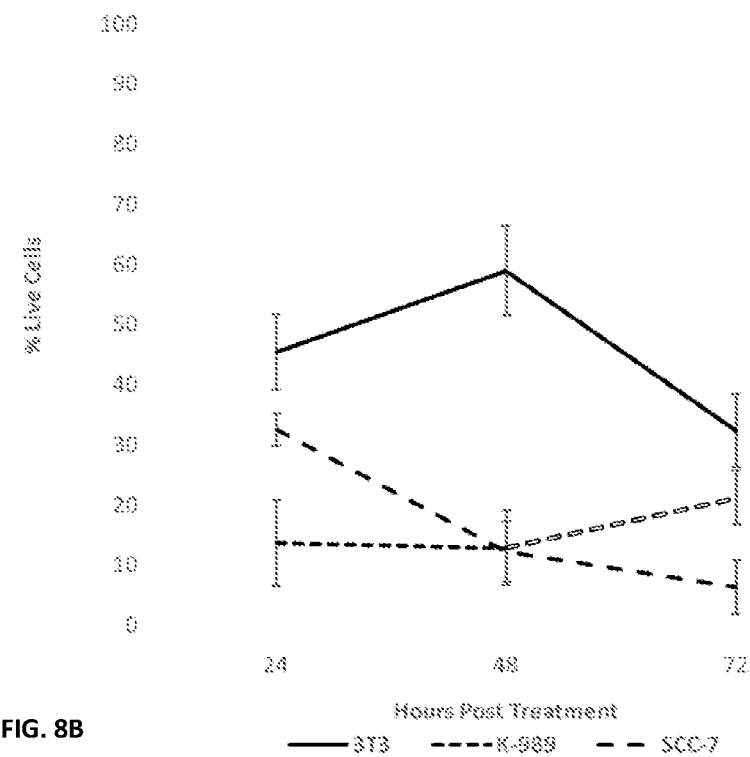

Selectivity of the NTP treatment is exemplified in FIGS. 8A and 8B. In this test, different cells types were treated with NTP. The cell types are Pancreatic cancer (K-989), Squamous-cell carcinoma (SCC-7), normal Schwan cells (SW-10), normal Bladder cells (HUC) shown in FIG. 8A and normal fibroblasts (3T3) shown in FIG. 8B. These tests used similar plasma parameters as shown with connection to FIGS. 7A and 7B.

FIG. 8A shows experimental results of treatment of different Cell populations as mentions. For each group, 100,000 cells were treated with NTP for 60 or 120 seconds. As control, cells were not treated. 24 hours post treatment, an XTT assay was performed to assess cell proliferation. As shown in these figures, NTP dose response varied for healthy and cancer cells. More specifically, at 60 seconds of NTP treatment, a selective effect of NTP treatment was noticed. At this time 93.14% of pancreatic cancer and 90.67% and squamous cell carcinoma cells were killed. In contrast, only 30.69% of normal bladder cells were killed, and 36.82% of normal schwan cells were killed ($p<0.05$ for both cancer vs. both healthy cells).

FIG. 8B shows relative cell numbers measured 24, 48 and 72 hours after treatment for 3T3 healthy fibroblasts, and the two cancerous cell line K989 and SCC-7. The cells were treated by NTP for 30 seconds. As controls, cells were treated with gas only (data not shown). As shown, the NTP response varied over time between healthy and cancer cells. Specifically, at 24, 48 and 72 hours, healthy 3T3 fibroblasts had 45.5%, 58.9% and 32.3% live cells respectively. Percent of live cells of K989 cells was 13.7%, 12.9% and 21.2% respectively, and of SCC-7 cells 32.6%, 12.23% and 6.4% respectively.

These results generally demonstrate that cancer cells are more sensitive to NTP treatment than healthy cells at 60 seconds of treatment. NTP toxicity effects healthy and cancer cells in a different dynamics, and at 48 hours, the toxic effect is minimal for healthy cells, but pronounced for cancer cells.

Figure 9:
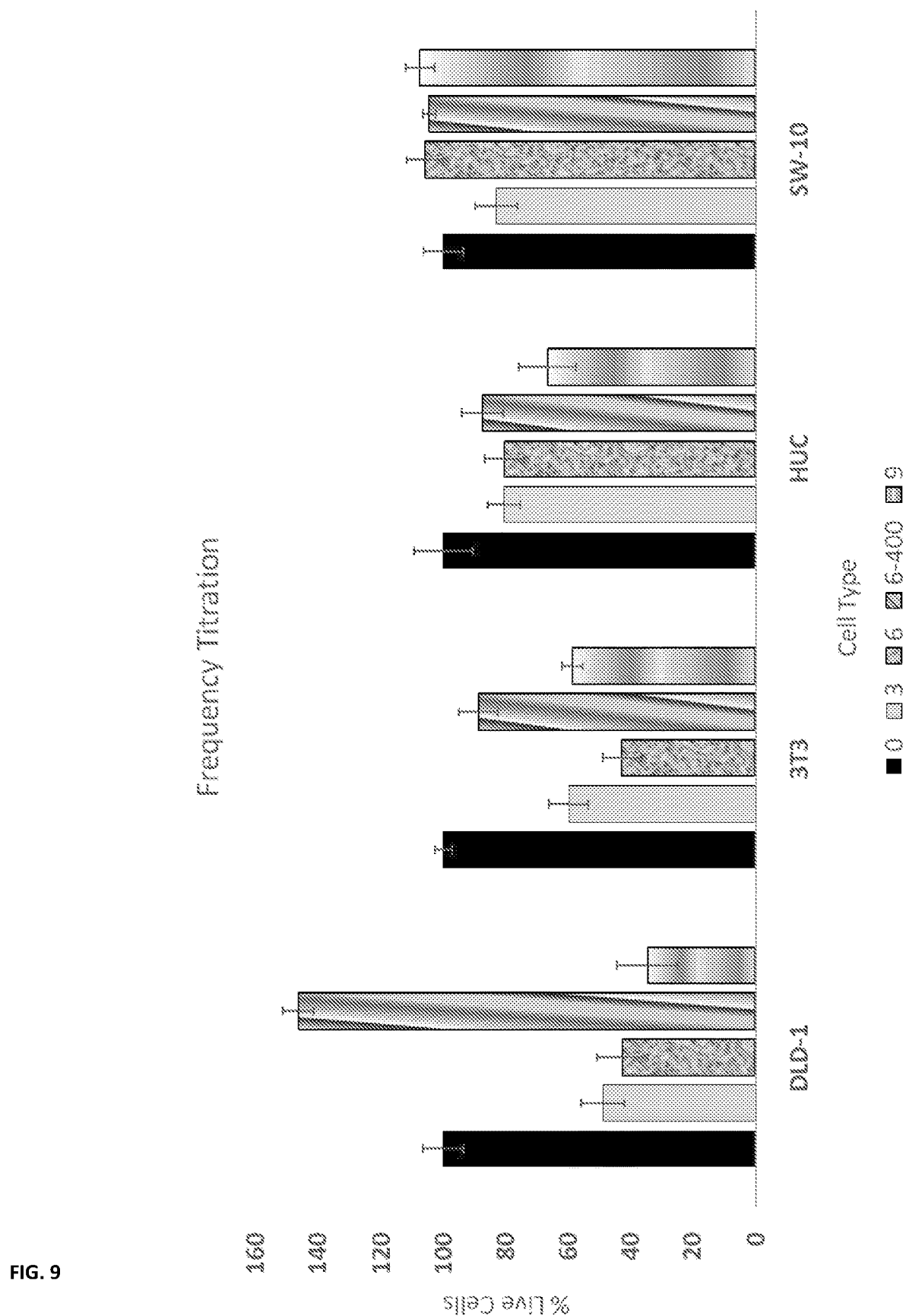
FIG. 9 shows a comparison between different repetition rates of plasma treatment according to some embodiments of the invention.

Reference is made to FIG. 9 showing a comparison between treatment techniques, differing in treatment time and in repetition rate of the NTP treatment. Four populations of cells were tested: DLD-1 colon Cancer cells, and healthy cells including HUC, 3T3 and SW-10. For each group, 100,000 cells were treated with NTP for 45 seconds, while repetition rate of NTP pulses varied as follows: 0=no treatment, 3=156 Hz, 6=217 Hz, 9=434 Hz. An additional cell group was tested with NTP repetition of 217 Hz and pulse duration 400 milliseconds instead of the 750 milliseconds for the rest of the samples, marked 6-400. 48 hours post treatment, an XTT assay was performed to assess cell proliferation showing the results in FIG. 9. All experiments were performed in Hexa-plicate. Plasma parameters for experiments are as follows: carrier frequency 1 MHz; peak voltage 850V; duty cycle 750 ms (or 400 ms); and Gas flow 3 L/min. Also, the plasma gun head was located 7 mm from the target cells. As shown in the figure, pulse duration of 400 milliseconds (group 6-400) provides almost no effect (NTP killing). Pulses of 750 milliseconds affected cancer cells in a linear manner, and proliferation rate reduced as repetition rate was increased. This linear correlation was not evident in healthy cells, were each cell type showed different sensitivity to NTP repetition rate. For a frequency of 434 Hz maximum selectivity was achieved between cancel and healthy cells. DLD-1 cancer cells displayed 65.4% cell death, while healthy cells displayed maximal death of 41.4% (3T3 fibroblasts).

Figure 10:
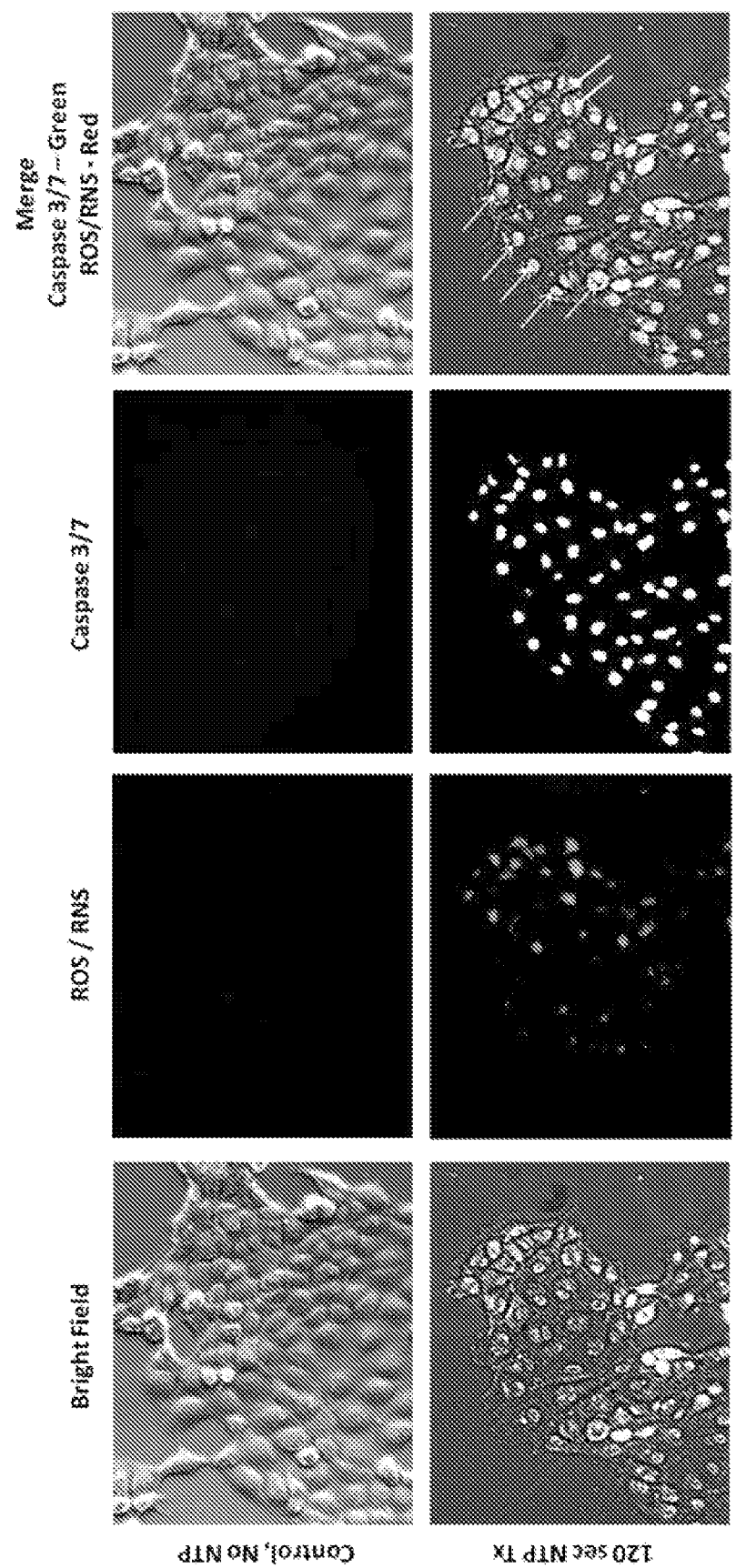
FIG. 10 show images of treated cancer and healthy cells exemplifying mechanism of cells death.

Reference is made to FIG. 10 comparing post NTP treatment reactions of Pancreatic cancer (K-989). The control cells were not treated by NTP and the test cells were by NTP for 120 seconds as previously described. 3 hours post treatment, cells were stained for Caspase 3/7 (marked with white arrows) and for reactive oxygen and nitrogen species (ROS and RNS respectively, while lines). Cells were observed in a fluorescent microscope at X40 magnification, and images were taken separately for the Caspase 3/7 and ROS and NRS using green and red filters respectively.

As shown, neither Caspase activation nor ROS/RNS were detected in the control group. In contrast, in treated cells Caspase 3/7 activation was shown, as staining of the cell's nuclei. ROS/RNS stains were detected only in a portion of the cells, shown by red cytoplasmic staining. Taken together these results indicate that NTP treatment causes cancer cell apoptosis as a mechanism of cells death. NTP treatment also causes ROS/RNS accumulation in cancer cells, although three hours post treatment, radical burden is not uniform.

Figure 11A:
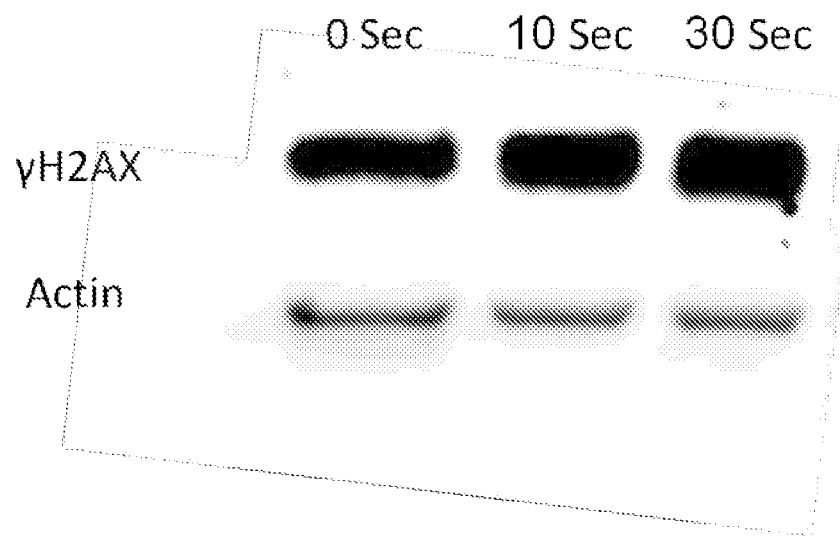
FIGS. 11A and 11B show experimental results of γH2AX treatment of NTP treated DLD-1 colon cancer cells.
Figure 11B:
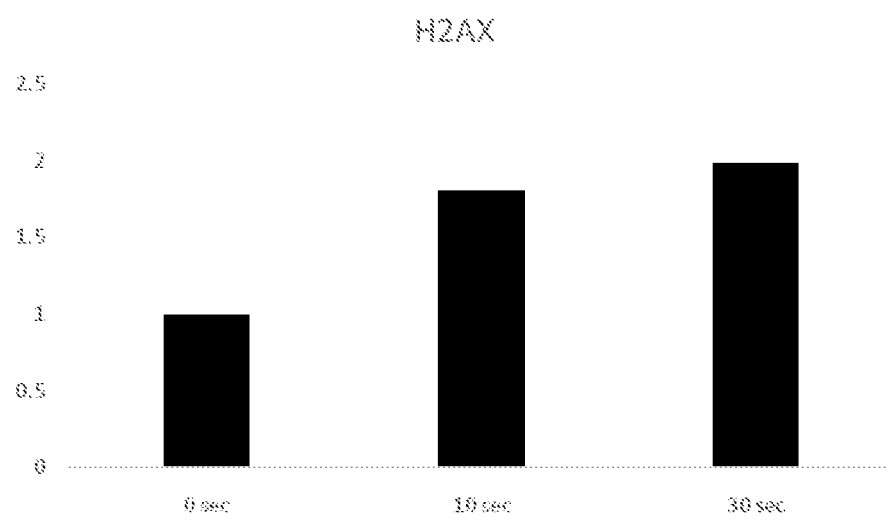

FIGS. 11A and 11B show experimental results of $\gamma$H2AX treatment of NTP treated DLD-1 colon cancer cells. FIG. 11A shows WB panel of the cells and FIG. 11B shows Quantification of $\gamma$H2AX.

In this experiment, DLD-1 cells were treated by NTP for 10 and 30 seconds as previously described, a group of control cells were not treated. 24 hours post treatment, cells were lysed, and western-blot was performed for $\gamma$H2AX. Histone H2AX phosphorylation on a serine 139 produces $\gamma$H2AX, a sensitive marker for DNA double-strand breaks (DSBs). To normalize the blot, Actin was blotted as control.

As shown, Colon cancer cells treated by NTP displayed DSB in a dose response manner: 10 seconds of NTP treatment caused increase in $\gamma$H2AX, and 30 seconds of treatment caused an even bigger increase. This indicates that NTP treatment causes DSB DNA breaks in a dose dependent fashion, similarly to the effect seen by ionizing radiation.

Figure 12A:
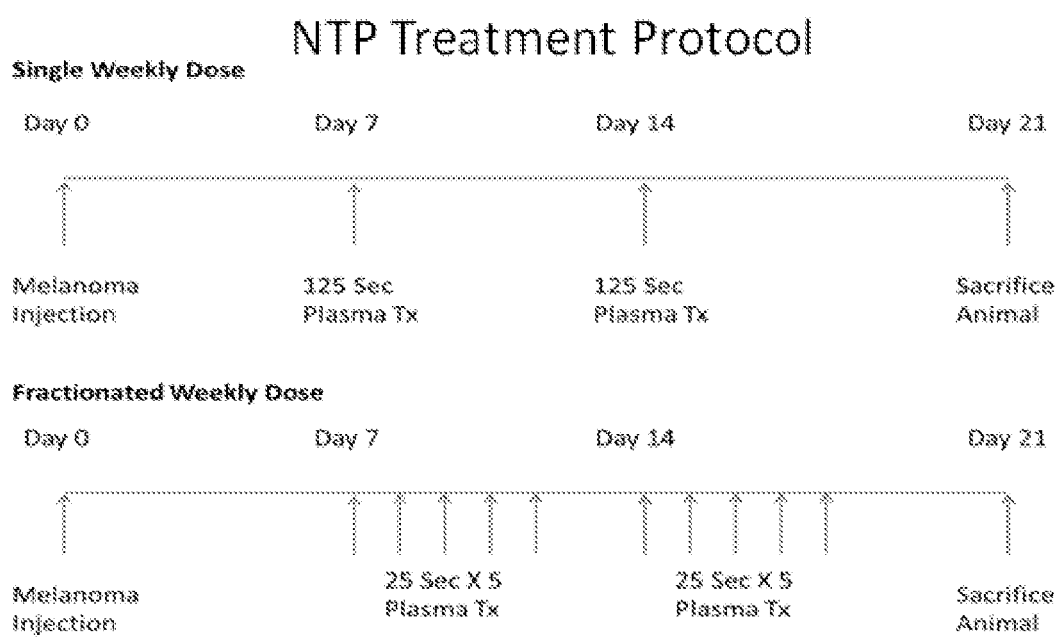
FIGS. 12A to 12E show in-vivo cold plasma treatment on melanoma cells in mice and comparison between two treatment protocols.
Figure 12B:
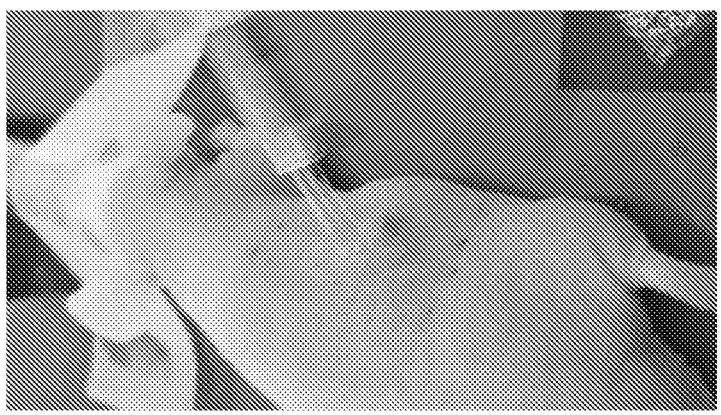
Figure 12C:
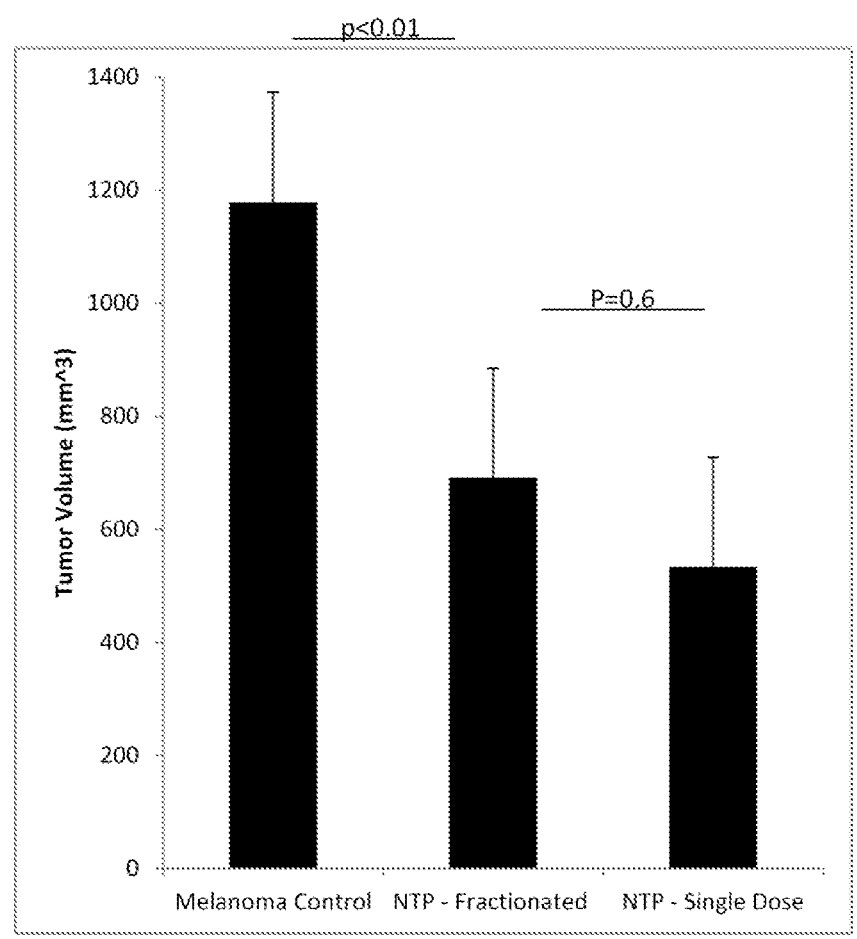
Figure 12D:
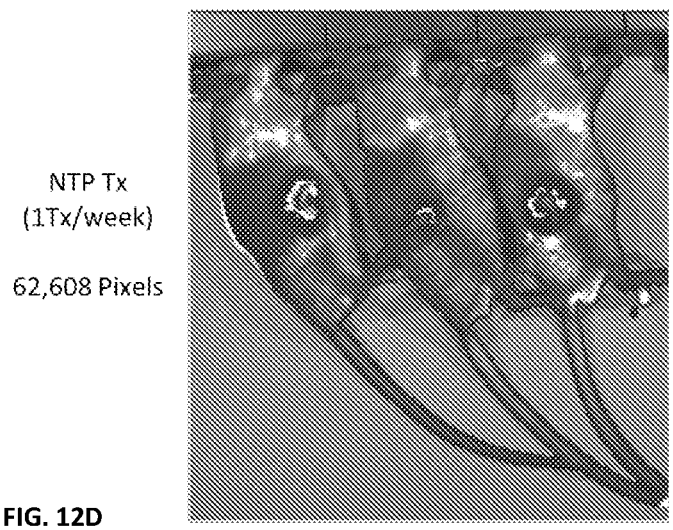
Figure 12E:
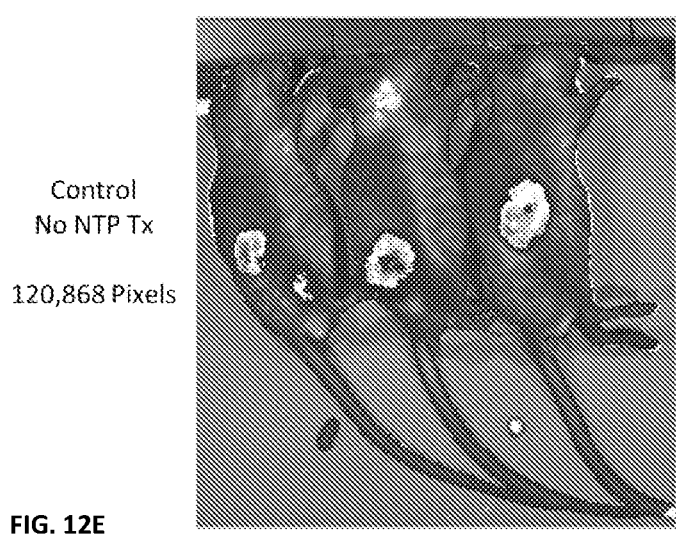

Reference is made to FIGS. 12A to 12E illustrating in-vivo melanoma treatment of melanoma B-16 cells in live mice using NTP. FIG. 12A illustrates treatment protocols used; FIG. 12B shows treatment applied on a mouse; FIG. 12C shows results of tumor reduction; FIGS. 12D and 12E show reduction in penetration of cancer to the epidermal layer post treatment.

The study design shown in FIG. 12A is as follows: On day 0, 1 million Melanoma cells were injected intra-dermally to 15 mice. At day 7, all tumors were of size larger than 7 mm in diameter. The study consisted of two treatment arms, both applying the same overall plasma dose: in the hypo-fractionated arm, 2 treatments 125 seconds each were applied, once each week. In the hyper-fractionated arm 10 treatments of 25 seconds each were applied. As controls mice bearing tumors were not treated. Another group of mice not bearing tumors were treated by the two protocols as control for NTP effect on normal skin. At the end of the study, mice were scanned with IVIS in order to estimate melanoma penetration to the surface of the skin (spectra: 500 nm Ex, 600 nm Em, where grey signal highlights melanoma skin penetration), tumors were measured, and all specimens were processed for pathological evaluation. FIG. 12B Shows part of the plasma treatment of a mouse with melanoma tumor. The black dots around the tumor are tattoos, used to mark NTP treatment area.

FIG. 12C shows results of both hypo and hyper fractionated NTP therapy leading to significant tumor volume reduction by 55% and 41% reduction respectively ($p<0.01$ independently). The difference between the two groups was not significant ($p=0.615$). FIGS. 12D and 12E show that epidermal layer penetration was reduced by 48.2% in the hypo fractionated treatment group (FIG. 12D) versus the control (FIG. 12E) showing the tumor at size of 62,608 pixels as compared to 120,868 pixels respectively ($p<0.01$).

Figure 13A:
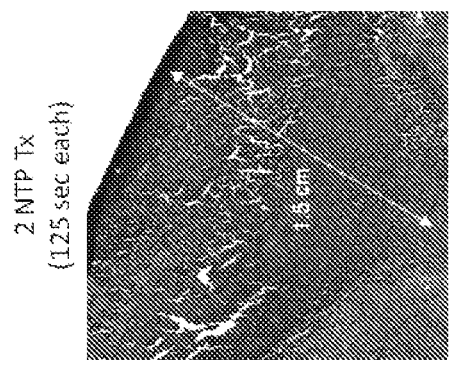
FIGS. 13A to 13F show the pathology results of treated cancer and healthy cells on mice.
Figure 13B:
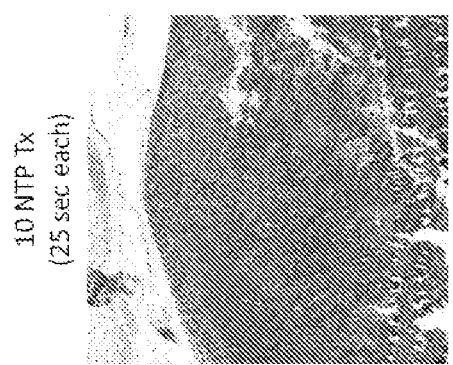
Figure 13C:
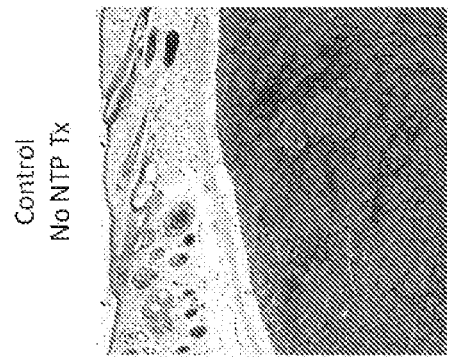
Figure 13D:
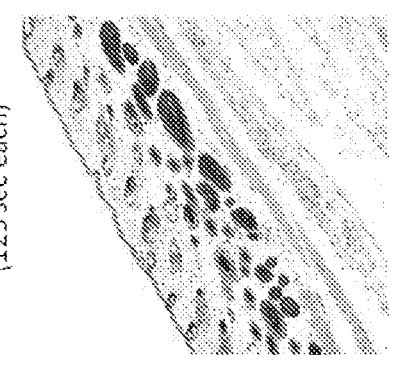
Figure 13E:
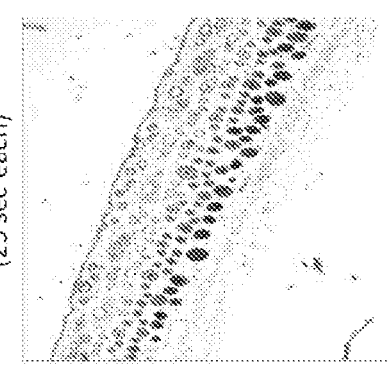
Figure 13F:
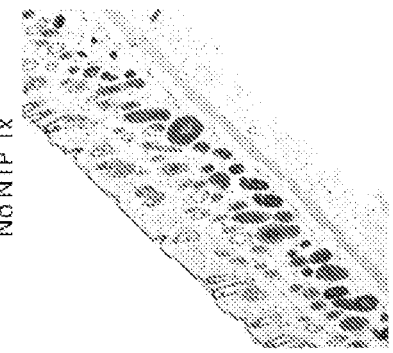

FIGS. 13A to 13F show the pathology results. In the untreated arm (FIG. 13C) no tumor necrosis was evident. In the hypo fractionated arm (FIG. 13A) uniform tumor necrosis was seen, penetrating 1.5 cm from the skin surface. In contrast, the hyper fractionated therapy (FIG. 13B) caused disperse areas of tumor necrosis. As also shown in FIGS. 13D to 13F both treatment protocols resulted in no apparent damage on normal skin.

The above shown our in-vivo results demonstrate that NTP treatment has a potent effect in-vivo, causing a drastic shrinkage of Melanoma tumors as well as other cancer types. Hypo fractionated treatment regimen resulted in slightly better efficacy, although statistically insignificant. On pathology on the other hand, marked differences were noted between the treatment arms, with marked a uniform tumor necrosis in the hypo fractionated arm, with a maximal penetration of 1.5 cm from skin surface. Most importantly, the normal skin was not affected by NTP treatment, strengthening the selective effect of NTP to cancer cells.

Thus, the present invention provides a novel system and technique of generating cold plasma. The technique and system of the invention provide controlled plasma generation with desired power and temperature enabling selective treatment of cancer and additional abnormal cells in-vivo and in-vitro.

The technique of the invention may also be used for treatment of any one of the following conditions: treatment of viral, bacteria, fungi and protozoal infections; treatment of artificial material or grafts; treatment of tumors or pre-malignant conditions; treatment of body tissue; treatment of inflammatory diseases; treatment of wounds; dental and peri-dental treatment; as well as cosmetic treatments of various types.

The system of the invention may utilize an endoscopic plasma treatment probe for local application of cold plasma within cavities of the treated human or animal. This is possible using long power-delivering electricity transmission channel, actually serving as a part of the resonant circuit of the RF oscillator. Thus, the use of the electricity transmission channel does not affect the frequency of plasma generation nor it induces losses to the system.

Additionally or alternatively, according to some embodiments, the present technique provides a special design of coaxial cable and plasma generating unit having metallic (e.g. silver) coated inner and outer electrodes, and Teflon insulation between them. The cable design yields negligibly small energy losses and thus drastically reduces heating of the cable and allows it to be safely placed inside the body. This significantly increases the efficiency of the operation of the system.

Further, according to some embodiments of the invention, the system utilizes a series of one or more RF pulses transferred by the coaxial cable or the transmission channel. According to some embodiments, the pulses are configured not be dangerous to the patient because the inner electrode is insulated and the outer electrode is grounded. In addition, the high frequency pulses assume high voltage for very short duration (e.g. a nanosecond time scale) and therefore are considerably safer to patients as larger voltage is required to obtain breakdowns as compared to long duration pulses. Such RF pulses having MHz frequency require lower voltage amplitudes to initiate the plasma compared to separated single voltage pulses or RF pulses at 10 kHz frequency, therefore adding safety to the device. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

The invention claimed is:

1. A system for generating cold plasma, the system comprising:
   a control unit connectable to an elongated member at a first proximal end of the elongated member;
   wherein said elongated member comprises:
      a plasma generating unit at a second distal end thereof and gas and
      an electricity transmission channel extending from said first proximal end towards said plasma generating unit;
   wherein the control unit comprises a gas supply unit configured to provide a selected gas composition through said gas transmission channel and a power supply unit configured to generate a selected sequence of high-frequency electrical pulses directed through said electricity transmission channel, thereby providing power and gas of said selected composition to the plasma generating unit for generating cold plasma; and
   wherein:
      said power supply unit comprises a resonance circuit configured for generating the high-frequency electrical pulses,
      said electricity transmission channel comprises a coaxial cable characterized by a self-impedance, and the coaxial cable is an element of the resonance circuit of the power supply unit which generates the high-frequency electrical pulses, the coaxial cable being electrically connected within the resonance circuit so that the self-impedance of the coaxial cable also serves as part of an impedance of the resonance circuit, the impedance acting to set a carrier frequency of the high-frequency electrical pulses.

2. The system of claim 1, wherein said power supply unit, electricity transmission channel and plasma generation unit are configured to prevent electrical discharge into surrounding thereof, thereby enabling use of said plasma generating unit on live biological tissue.

3. The system of claim 2, wherein said selected sequence of high frequency electrical pulses consists of a sequence of pulses having a repetition rate between 100 Hz and 600 Hz and carrier frequency between 500 kHz and 10 MHz and having peak voltage between 0.5 kV and 2 kV.

4. The system of claim 1, wherein said selected sequence of high frequency pulses consists of a sequence of pulses having a pulse duration between 450 µs and 800 µs.

5. The system of claim 1, wherein said electricity transmission channel is configured for preventing electricity discharge and electromagnetic radiation into surrounding thereof to thereby prevent damage to surrounding biological tissue.

6. The system of claim 5, wherein said electricity transmission channel is configured as a coaxial electricity transmission cable having an internal conductor configured to carry electricity signal and an external conductor shielding between an electrical potential in said internal conductor and a surrounding of the cable; said external conductor is kept at ground potential.

7. The system of claim 1, wherein said gas supply unit is configured to supply a predetermined flow of gas having a Penning mixture along said gas transmission channel, thereby providing said gas mixture having low breakdown threshold.

8. The system of claim 7, wherein said Penning gas mixture is a mixture of Neon and Argon gasses with ratio between 98:2 and 99.9:0.1 of Ne:Ar.

9. The system of claim 1, wherein said elongated member, including said gas and electricity transmission channels thereof, is flexible.

10. The system of claim 1, wherein said elongated member comprises a distal portion, said distal portion being rigid thereby enabling direction of the distal end to a desired location.

11. The system of claim 1, wherein said elongated member is configured to be inserted into a working channel of an endoscope for selectively generating cold plasma within a cavity of a biological tissue.

12. The system of claim 1, wherein said elongated member further comprises one or more sensors mounted at said second distal end thereof, and said one or more sensors comprise at least one of the following: thermal sensor, spectrometry sensor, optical sensor, photo-spectrometer sensor, electric field sensor and magnetic field sensor.

13. The system of claim 1, wherein said plasma generating unit, located at said second distal end of the elongated member, is configured as a dielectric barrier discharge plasma generating unit and comprises a first internal electrode providing electrical potential and a second external electrode, at least one of said first and second electrode is covered by a dielectric layer of predetermined thickness; potential difference between said first and second electrodes cause electrical discharge through gas flowing between said first and second electrodes to thereby generate said plasma.

14. The system of claim 1, configured for generating cold plasma being characterized in having a temperature below 50° C.

15. The system of claim 1, wherein said plasma generating unit, when operated with input gas and electric pulses, generates a plasma plume having a length beyond an exit aperture of the plasma generating unit of between 2 mm and 20 mm.

16. The system of claim 1, configured for use in treatment of cancer in living tissue.

17. The system of claim 1, wherein said elongated member is configured to be directed to apply cold plasma at natural or surgically made cavities in living organisms.

18. The system of claim 1, wherein said gas supply unit is configured to supply a predetermined flow of helium along said gas transmission channel.

19. The system of claim 1, wherein said elongated member is configured to be inserted into a working channel of a flexible endoscope for selectively generating cold plasma within an existing natural cavity of a biological tissue accessed through an existing natural orifice.

20. The system of claim 1, wherein damage producing a change in the capacitance of the coaxial cable changes the tuning of the resonance circuit.

21. The system of claim 1, wherein the coaxial cable is electrically connected within the resonance circuit as a capacitance element.

22. A method for generating cold plasma within a biological cavity, the method comprising:
providing a flow of gas of predetermined material composition and predetermined flow rate through an elongated transmission channel to a desired location within said biological cavity;
generating, using a carrier frequency selected by a resonance circuit characterized by an associated impedance, a series of high frequency electrical pulses and transmitting said series through a shielded electricity transmission channel comprising a coaxial cable to said desired location; and
allowing discharge of potential difference resulting from said series of high frequency electrical pulses through said gas flow at close proximity to said desired location with the biological cavity, thereby generating cold plasma flow directed at said desired location;
wherein the coaxial cable is an element of the resonance circuit, electrically connected within the resonance circuit so that a self-impedance of the coaxial cable also serves as part of the impedance of the resonance circuit, tuning it to generate the carrier frequency.

23. The method of claim 22, wherein the resonance circuit has a resonant frequency between 0.5 MHz and 10 MHz.

24. A cold plasma generator comprising:
a pulse generating circuit, configured to generate electric pulses by oscillation at a radio-range carrier frequency;
a transmission channel configured to transmit the generated pulses into a plasma-generating electrical field between two conductors separated by a dielectric material;
a gas transmission channel, configured to deliver gas to the transmission channel for conversion into plasma by the plasma-generating electrical field; and
a coaxial cable, wherein:
the two conductors of the transmission channel comprise inner and outer conductors of the coaxial cable; and
the coaxial cable is an element of a resonance circuit of the pulse generating circuit, electrically connected within the resonance circuit so that a self-impedance of the coaxial cable serves as part of an impedance of the resonant circuit which selects the carrier frequency of the electric pulses.

25. The system of claim 24, wherein the coaxial cable serves as an operating element of both the pulse generating circuit and the electrical transmission channel.

* * * * *